United States Patent
Silveira et al.

(10) Patent No.: US 11,324,583 B1
(45) Date of Patent: May 10, 2022

(54) MULTI-LUMEN STENT-GRAFT AND RELATED SURGICAL METHODS

(71) Applicant: Archo Medical LTDA, Florianópolis (BR)

(72) Inventors: Pierre Galvagni Silveira, Florianópolis (BR); Andrea Piga Carboni, Florianópolis (BR)

(73) Assignee: Archo Medical LTDA, Florianópolis (BR)

( * ) Notice: Subject to any disclaimer, the term of this patent is extended or adjusted under 35 U.S.C. 154(b) by 0 days.

(21) Appl. No.: 17/497,199

(22) Filed: Oct. 8, 2021

Related U.S. Application Data

(60) Provisional application No. 63/203,046, filed on Jul. 6, 2021.

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2002/077* (2013.01); *A61F 2250/0039* (2013.01)

(58) Field of Classification Search
CPC .................. A61F 2/07; A61F 2002/061; A61F 2250/0039
See application file for complete search history.

(56) References Cited

U.S. PATENT DOCUMENTS

| | | |
|---|---|---|
| 5,385,580 A | 1/1995 | Schmitt |
| 5,389,106 A | 2/1995 | Tower |
| 5,464,449 A | 11/1995 | Ryan et al. |
| 5,522,881 A * | 6/1996 | Lentz ........................ A61F 2/07 623/1.13 |
| 5,575,817 A | 11/1996 | Martin |
| 5,632,772 A | 5/1997 | Alcime et al. |
| 5,643,340 A | 7/1997 | Nunokawa |
| 5,653,743 A | 8/1997 | Martin |
| 5,653,747 A | 8/1997 | Dereume |
| 5,713,948 A | 2/1998 | Uflacker |
| 5,718,973 A | 2/1998 | Lewis et al. |
| 5,755,773 A | 5/1998 | Evans et al. |
| 5,769,887 A | 6/1998 | Brown et al. |
| 5,800,514 A | 9/1998 | Nunez et al. |
| 5,824,040 A | 10/1998 | Cox et al. |
| 5,855,598 A | 1/1999 | Pinchuk |
| 5,906,641 A | 5/1999 | Thompson et al. |
| 5,984,955 A | 11/1999 | Wisselink |

(Continued)

FOREIGN PATENT DOCUMENTS

| | | |
|---|---|---|
| AU | 2007240703 B2 | 2/2012 |
| AU | 2008343933 B2 | 1/2013 |

(Continued)

*Primary Examiner* — Brian E Pellegrino
(74) *Attorney, Agent, or Firm* — Knobbe, Martens, Olson & Bear, LLP

(57) ABSTRACT

A multi-lumen stent-graft including a graft portion and a stent frame. The stent-graft includes multiple through-channels formed of the graft portion. The graft portion can comprise a PTFE material and the through-channels can be formed of fused portions of the graft portion. The stent-graft can be used in a prostheses that connects multiple vessel branches such as for the repair of aortic aneurysms or other vessels of the body.

17 Claims, 25 Drawing Sheets

(56) References Cited

U.S. PATENT DOCUMENTS

| | | |
|---|---|---|
| 6,015,431 A | 1/2000 | Thornton et al. |
| 6,030,415 A | 2/2000 | Chuter |
| 6,059,824 A | 5/2000 | Taheri |
| 6,068,654 A | 5/2000 | Berg |
| 6,344,056 B1 | 2/2002 | Dehdashtian |
| 6,451,033 B1 | 9/2002 | Berg et al. |
| 6,579,314 B1 | 6/2003 | Lombardi et al. |
| 6,645,242 B1 | 11/2003 | Quinn |
| 6,660,015 B1 | 12/2003 | Berg et al. |
| 6,673,102 B1 | 1/2004 | Vonesh et al. |
| 7,122,052 B2 | 10/2006 | Greenhalgh |
| 7,520,895 B2 | 4/2009 | Douglas et al. |
| 7,575,586 B2 | 8/2009 | Berg et al. |
| 7,901,449 B2 | 3/2011 | Goicoechea et al. |
| 8,092,511 B2 | 1/2012 | Chuter et al. |
| 8,734,504 B2 | 2/2014 | Kelly |
| 8,845,714 B2 | 9/2014 | DiMatteo et al. |
| 9,066,793 B2 | 6/2015 | Hung et al. |
| 9,370,413 B2 | 6/2016 | Kelly |
| 9,770,320 B2 | 9/2017 | Eells |
| 9,925,032 B2 | 3/2018 | Jensen et al. |
| 9,949,818 B2 | 4/2018 | Kelly |
| 10,350,052 B2 | 7/2019 | Kelly |
| 10,588,735 B2 | 3/2020 | Drake et al. |
| 10,952,838 B2 | 3/2021 | Frid |
| 2001/0004707 A1 | 6/2001 | Dereume et al. |
| 2002/0052648 A1 | 5/2002 | McGuckin et al. |
| 2002/0198585 A1 | 12/2002 | Wisselink |
| 2004/0068277 A1 | 4/2004 | Solem |
| 2004/0078053 A1 | 4/2004 | Berg et al. |
| 2004/0093031 A1 | 5/2004 | Burkhart et al. |
| 2004/0193254 A1 | 9/2004 | Greenberg et al. |
| 2005/0113905 A1 | 5/2005 | Greenberg et al. |
| 2005/0113909 A1* | 5/2005 | Shannon ................ A61F 2/07 623/1.46 |
| 2006/0136046 A1 | 6/2006 | Hartley et al. |
| 2007/0135903 A1 | 6/2007 | Gregorich et al. |
| 2008/0167704 A1 | 7/2008 | Wright et al. |
| 2008/0221668 A1* | 9/2008 | Pinchuk ................ A61F 2/07 623/1.23 |
| 2008/0269866 A1 | 10/2008 | Hamer et al. |
| 2009/0030502 A1 | 1/2009 | Sun et al. |
| 2009/0048663 A1 | 2/2009 | Greenberg |
| 2009/0171441 A1 | 7/2009 | Osborne |
| 2009/0182406 A1 | 7/2009 | Eidenschink |
| 2010/0036397 A1 | 2/2010 | Kang et al. |
| 2011/0054594 A1 | 3/2011 | Mayberry et al. |
| 2013/0144373 A1 | 6/2013 | Shahriari |
| 2014/0371836 A1 | 12/2014 | Silveira et al. |
| 2016/0120667 A1 | 5/2016 | Bolduc et al. |
| 2017/0181838 A1 | 6/2017 | Eller et al. |
| 2017/0367855 A1* | 12/2017 | Jenni ..................... A61F 2/07 623/1.13 |
| 2018/0206972 A1 | 7/2018 | Arbefeuille et al. |
| 2018/0214259 A1 | 8/2018 | Spindler et al. |
| 2019/0321161 A1* | 10/2019 | Teßarek .................. A61F 2/07 623/1.13 |
| 2019/0380851 A1 | 12/2019 | Bertini et al. |
| 2020/0306064 A1 | 10/2020 | Perkins et al. |
| 2020/0330214 A1 | 10/2020 | Ryan |

FOREIGN PATENT DOCUMENTS

| | | |
|---|---|---|
| AU | 2017270374 B2 | 5/2021 |
| CN | 201333110 Y | 10/2009 |
| CN | 201333111 Y | 10/2009 |
| CN | 209661880 U | 11/2019 |
| DE | 102017120819 A1 | 3/2019 |
| EP | 1157674 B1 | 7/2005 |
| EP | 2326282 | 6/2011 |
| EP | 1759666 B1 | 7/2011 |
| EP | 2799038 B1 | 10/2016 |
| EP | 2999429 B1 | 7/2018 |
| EP | 3069670 B1 | 7/2019 |
| EP | 3785665 A1 | 3/2021 |
| JP | 2008055226 A | 3/2008 |
| JP | 4278988 B2 | 6/2009 |
| JP | 4575451 B2 | 11/2010 |
| JP | 5574123 B2 | 8/2014 |
| JP | 2017503607 A | 2/2017 |
| JP | 2018509977 A | 4/2018 |
| WO | WO 1995/026695 A2 | 10/1995 |
| WO | WO 2001/021095 A2 | 3/2001 |
| WO | WO 2001/049211 A1 | 7/2001 |
| WO | WO 2002/022055 A2 | 3/2002 |
| WO | WO 2005/030096 A1 | 4/2005 |
| WO | WO 2006/034340 A1 | 3/2006 |
| WO | WO 2006/076441 A1 | 7/2006 |
| WO | WO 2007/025101 A2 | 3/2007 |
| WO | WO 2007/026991 A1 | 3/2007 |
| WO | WO 2009/020653 A1 | 2/2009 |
| WO | WO 2013/040663 A1 | 3/2013 |
| WO | WO 2019/042201 A1 | 3/2019 |
| WO | WO 2019/101075 A1 | 5/2019 |

* cited by examiner

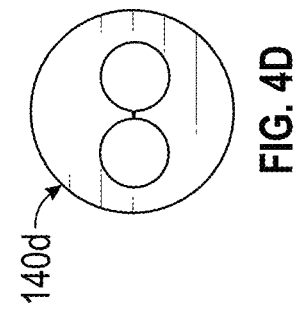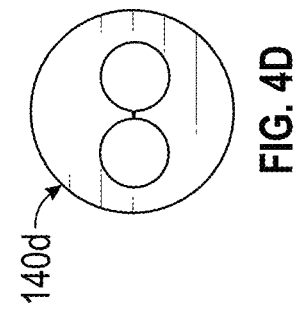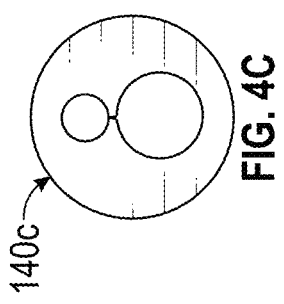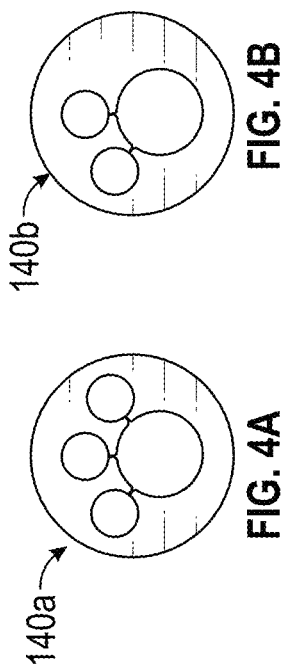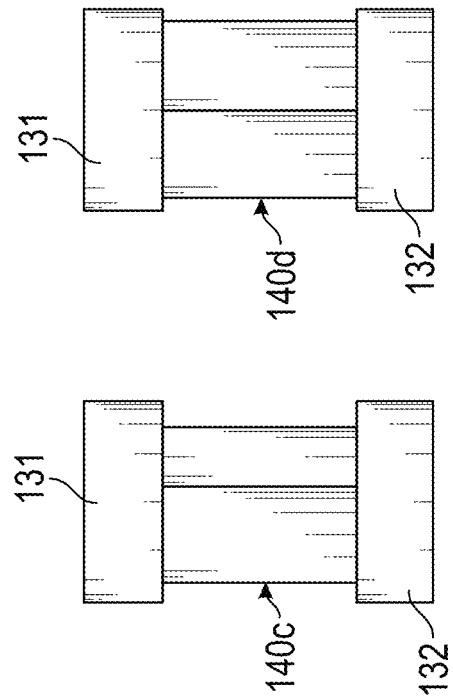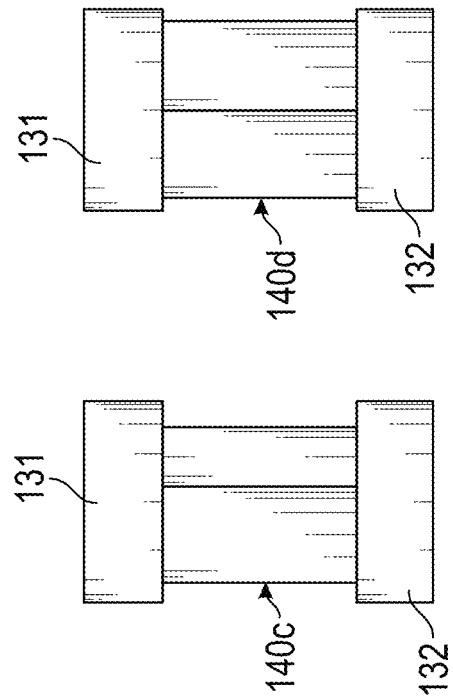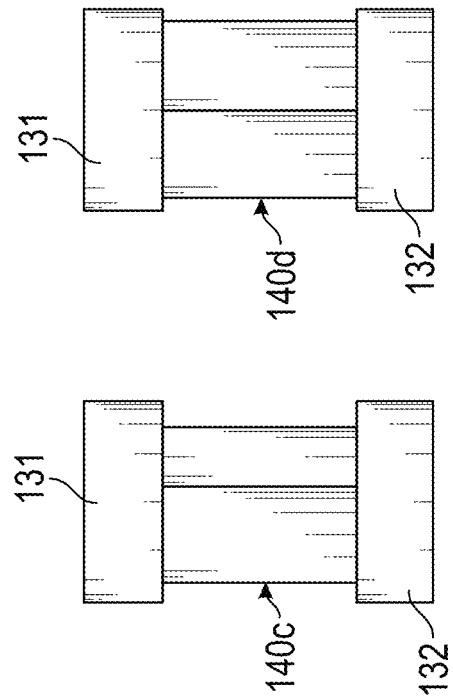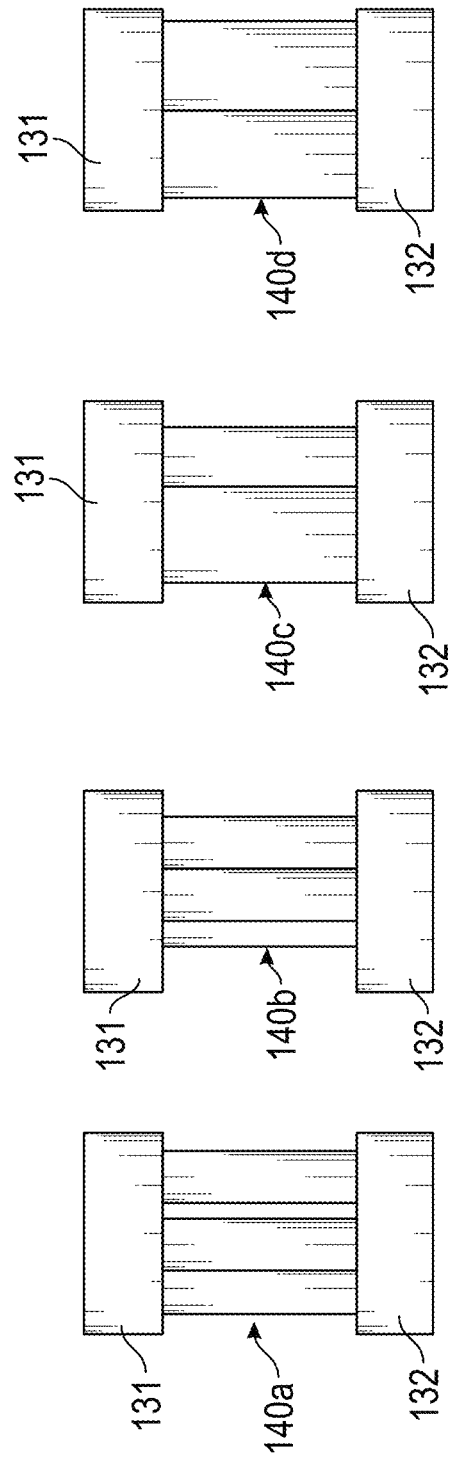

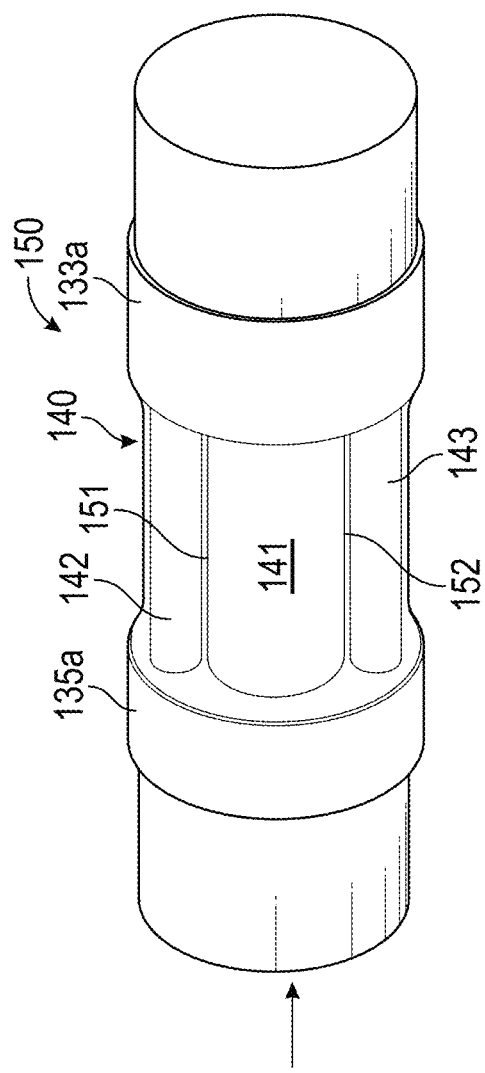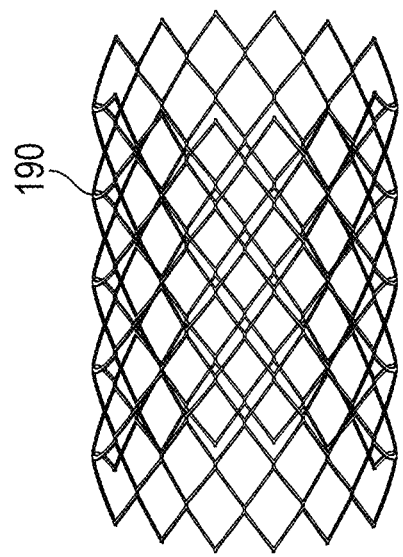
FIG. 12

MULTI-LUMEN STENT-GRAFT AND RELATED SURGICAL METHODS

BACKGROUND

Field

This disclosure generally relates to stent-grafts and related methods and techniques for implantation within a human or animal body for the repair of damaged vessels, ducts or other passageways.

Related Art

The vessels and ducts within a human or animal body, such as blood vessels, may occasionally weaken or increase in diameter and can eventually rupture. An example of this is an aortic aneurysm that includes an abnormal dilation of the wall of the aorta. Over time and exposure to the pressure of hemodynamic forces, an aneurysm can rupture and cause fatal hemorrhaging. One surgical intervention for an aneurysm or other weakened or ruptured vessel includes the use of an endoluminal prosthesis such as a graft to provide some or all the functionality of the original healthy vessel and particularly to reduce hemodynamic forces on the aneurysm. U.S. Patent Pub. 2014/0371836, provides examples of apparatus and surgical techniques for bridging an aneurysm within the thoracic aorta.

SUMMARY

According to a first aspect, a multi-lumen expandable stent-graft including a graft sleeve of a single tube of polymer material that forms first, second and third parallel flow channels between a first open end and a second open end. A self-expanding wire stent is coaxially mounted over the graft sleeve and affixed to said graft sleeve at the first and second open ends. The first flow channel is formed by a first linear connected segment of the polymer material channel. The first linear connected segment aligns parallel with a longitudinal axis of the stent-graft and includes inlet and outlet ports spaced inwardly from the first and second open ends of the graft sleeve. The second flow channel is formed by a second linear connected segment of the polymer material channel. The second linear connected segment aligns parallel with the longitudinal axis of the stent-graft and includes inlet and outlet ports spaced inwardly from the first and second open ends of the graft sleeve. The third flow channel is formed by a third linear connected segment of the polymer material channel. The third linear connected segment aligns parallel with the longitudinal axis of the stent-graft, and includes inlet and outlet ports spaced inwardly from the first and second open ends of the graft sleeve. The polymer material of the graft sleeve is or includes Polytetrafluoroethylene (PTFE) and the first, second, and third linear connected segments comprise fused portions of the PTFE material. A total circumference of each of the flow channels and any connecting segments is approximately equal to a circumference of the single tube of polymer material.

According to a second aspect, a multi-lumen expandable stent-graft includes a graft sleeve with polymer material forming first, second and third flow channels between a first open end and a second open end. A self-expanding wire stent coaxially mounts over the graft sleeve and affixes to said graft sleeve at the first and second open ends. The first flow channel is formed by a first linear connected segment of the polymer material channel. The first linear connected segment is aligned parallel with a longitudinal axis of the stent-graft and includes inlet and outlet ports spaced inwardly from the first and second open ends of the graft sleeve. The second flow channel is formed by a second linear connected segment of the polymer material channel. The second linear connected segment is aligned parallel with the longitudinal axis of the stent-graft and includes inlet and outlet ports spaced inwardly from the first and second open ends of the graft sleeve. The third flow channel is formed by a third linear connected segment of the polymer material channel. The third linear connected segment is aligned parallel with the longitudinal axis of the stent-graft and includes inlet and outlet ports spaced inwardly from the first and second open ends of the graft sleeve.

According to another aspect, the first, second, and third channels are parallel. According to another aspect, the first, second, and third flow channels are unsupported by the self-expanding wire stent. According to another aspect, the first and second open ends each include a cylindrical wall portion supported by the self-expanding wire stent. According to another aspect, respective ends of the first, second, and third linear connected segments are spaced inwardly from the first and second open ends. According to another aspect, the first and second open ends include folded portions of the polymer material. According to another aspect, the first and second open ends include an additional layer of the polymer material that encapsulates first and second ends of the stent portion. According to another aspect, the graft sleeve comprises a single tube of the polymer material and a total circumference of each of the flow channels is equal to a circumference of the single tube of polymer material. According to another aspect, the polymer material of the graft sleeve comprises Polytetrafluoroethylene (PTFE) and the first, second, and third linear connected segments comprise fused portions of the PTFE material. According to another aspect, the fused portions of the PTFE material are formed by melting the PTFE material above a melting temperature thereof. According to another aspect, the fused portions of the PTFE material are formed by ultrasonic welding. According to another aspect, the fused portions of the first linear connected segment include an intermediate layer of PTFE material. According to another aspect, the first open end has a length that is between 2 and 5 times greater than a length of the second open end. According to another aspect, a channel length of the first, second, and third channels is between 50% and 90% of a hub length extending from an upper rim of the first open end to a lower rim of the second open end. According to another aspect, a channel length of the first, second, and third channels is between 75% and 90% of a hub length extending from an upper rim of the first open end to a lower rim of the second open end. According to another aspect, a first diameter of the first flow channel is within 10% to 40% of a sleeve diameter of the first and second open ends, a second diameter of the second flow channel is within 10% to 40% of the sleeve diameter, and a third diameter of the third flow channel is within 50% to 80% of the sleeve diameter. According to another aspect, a first diameter of the first flow channel is within 5% to 25% of a sleeve diameter of the first and second open ends, a second diameter of the second flow channel is within 5% to 25% of the sleeve diameter, a third diameter of the third flow channel is within 5% to 25% of the sleeve diameter and a fourth diameter of a fourth flow channel is within 50% to 75% of the sleeve diameter.

According to a third aspect, an expandable stent-graft includes a graft sleeve having Polytetrafluoroethylene (PTFE) material forming a main fluid flow channel between a first open end and a second open end of said graft sleeve and including an external surface and an internal surface. A first internal channel and a second internal channel are formed within the graft sleeve and each include inlet and outlet ports spaced inwardly from the first and second open ends of the graft sleeve. The first and second internal flow channels are separated by a linear connected segment aligned along a longitudinal axis of the graft sleeve. The linear connected segment is formed of fused portions of the internal surface of the PTFE material of the graft sleeve. A self-expanding wire stent is coaxially mounted over the graft sleeve and affixed to said graft sleeve at the first and second open ends.

According to another aspect, the first and second internal flow channels are unsupported by the self-expanding wire stent. According to another aspect, the first and second open ends each include a cylindrical wall portion supported by the self-expanding wire stent. The inlet and outlet ports are spaced inwardly from the respective cylindrical wall portion. According to another aspect, first and second ends of the linear connected segment are spaced inwardly from respective cylindrical wall portions of the graft sleeve. According to another aspect, the cylindrical wall portions include folded portions of the PTFE material. According to another aspect, the graft sleeve comprises a single tube of PTFE material and a total circumference of each of the flow channels is equal to a circumference of the single tube of polymer material. According to another aspect, the fused portions of the internal surface of the PTFE material are formed by melting the PTFE material above a melting temperature thereof. According to another aspect, the fused portions of the internal surface of the PTFE material are formed by ultrasonic welding. According to another aspect, the first and second channels each comprise cylindrical wall portions. According to another aspect, a channel length of the first and second channels is between 50% and 90% of a hub length extending from an upper rim of the first open end to a lower rim of the second open end. According to another aspect, a channel length of the first and second channels is between 75% and 90% of a hub length extending from an upper rim of the first open end to a lower rim of the second open end. According to another aspect, a first diameter of the first flow channel is within 20% to 50% of a sleeve diameter of the first and second open ends and a second diameter of the second flow channel is within 50% to 80% of the sleeve diameter.

According to a fourth aspect, a method of making an expandable stent-graft includes positioning a graft sleeve including Polytetrafluoroethylene (PTFE) material over a body of a mandrel. The mandrel includes a central portion including a first channel mandrel and a second channel mandrel. Longitudinal axes of the first and second channel mandrels align with a longitudinal axis of the mandrel. A first portion of a first side of the graft sleeve is inserted between the first and second channel mandrels and pushed into contact with a second portion of a second side of the graft sleeve. The first and second portions of the graft sleeve are fused to form a linear connected segment aligned along the longitudinal axis of the mandrel. The linear connected segment divides a central portion of the graft sleeve into a first internal channel and a second internal channel formed within the graft sleeve. The graft sleeve can be removed from the mandrel.

According to a further aspect, a self-expanding wire stent is coaxially mounted over the graft sleeve while still on the mandrel. The self-expanding wire stent is affixed with the first and second open ends of the graft sleeve. According to another aspect, an end portion of the graft sleeve is folded over an end portion of the self-expanding wire stent. According to another aspect, an end portion of the self-expanding wire stent is encapsulating between an additional PTFE material and the graft sleeve. According to another aspect, the linear connected segment is formed by melting the PTFE material above a melting temperature thereof. According to another aspect, the linear connected segment is formed by ultrasonic welding. According to another aspect, the first and second channel mandrels are detachable from the body of the mandrel. According to another aspect, the first and second channel mandrels each comprise a cylindrical member having a diameter corresponding to a diameter of the respective first and second channels. According to another aspect, an intermediate layer of PTFE material is included between the first portion of the first side of the graft sleeve and the second portion of the second side of the graft sleeve to form the linear connected segment.

According to a fifth aspect, a method of surgically implanting a prostheses for treatment of a branched vessel includes positioning a first stent-graft hub having a primary flow channel. A first flow channel and a second flow channel are proximate a treatment location. A hub guide wire is inserted within the branched vessel. A catheter is advanced along the hub guide wire. A first stent-graft hub is deployed using the catheter. The treatment location along the branched vessel is bridged with a primary graft tube, including advancing a primary catheter within the primary flow channel. A first end of the primary graft tube is deployed within the primary flow channel. A second end of the primary graft tube is deployed within the branched vessel with the primary catheter. The treatment location is bridged between the first stent-graft hub and a first branch of the branched vessel with a first graft tube. This includes inserting a first guide wire through the first branch of the branched vessel and into the first flow channel of the first stent-graft hub, advancing a first catheter along the first guide wire, deploying a first end of the first graft tube within the first flow channel, and deploying a second end of the first graft tube within the first branch with the first catheter. The treatment location is bridged between the first stent-graft hub and a second branch of the branched vessel with a second graft tube. This includes inserting a second guide wire through the second branch of the branched vessel and into the second flow channel of the second stent-graft hub, advancing a second catheter along the second guide wire, and deploying a first end of the second graft tube within the second flow channel and a second end of the second graft tube within the second branch with the second catheter.

According to another aspect, further including bridging the treatment location between the first stent-graft hub and a third branch of the branched vessel with a third graft tube, including inserting a third guide wire through the third branch of the branched vessel and into a third flow channel of the first stent-graft hub, and advancing a third catheter along the third guide wire, and deploying a first end of a third graft tube within the third flow channel and a second end of the third graft tube within the third branch. According to another aspect, further including positioning a second stent-graft hub having a primary flow channel and a first flow channel on an opposite side of the treatment location from the first stent-graft hub. Bridging the treatment location along the branched vessel with the primary graft tube by deploying the second end of the primary graft tube within the primary flow channel of the second stent-graft hub. According to another aspect, further including bridging the treatment location between the second stent-graft hub and a third branch of the branched vessel with a third graft tube, by inserting a third guide wire through the third branch of the branched vessel and into the first flow channel of the second stent-graft hub, advancing a third catheter along the third guide wire, and deploying a first end of a third graft tube within the first flow channel of the second stent-graft hub and a second end of the third graft tube within the third branch.

According to sixth aspect, a multi-lumen expandable stent-graft has a graft sleeve formed of a single tube of polymer material having a sleeve diameter. A first open end includes first cylindrical wall having an upper rim. A second open end includes a second cylindrical wall having a lower rim. The first open end is spaced apart from the second open end along a longitudinal axis. A hub length extends from the upper rim of the first open end to the lower rim of the second open end. A plurality of parallel flow channels extends between the first open end and the second open end and defines a channel length therebetween. The channel length is between 50% and 90% of the hub length. A first flow channel is formed by a first linear connected segment of the polymer material channel and includes inlet and outlet ports in communication with the respective first and second open ends of the graft sleeve. The first linear connected segment aligns parallel with the longitudinal axis of the stent-graft. The first linear connected segment includes a first width. A second flow channel is formed by a second linear connected segment of the polymer material channel and includes inlet and outlet ports in communication with the respective first and second open ends of the graft sleeve. The second linear connected segment aligns parallel with the longitudinal axis of the stent-graft. The second linear connected segment includes a second width. A third flow channel is formed by a third linear connected segment of the polymer material channel and includes inlet and outlet ports in communication with the respective first and second open ends of the graft sleeve. The third linear connected segment aligns parallel with the longitudinal axis of the stent-graft. The third linear connected segment having a third width. A fourth flow channel is formed by the first, second, and third linear connected segments of the polymer material channel and includes inlet and outlet ports in communication with the respective first and second open ends of the graft sleeve. A self-expanding wire stent coaxially mounts over the graft sleeve and affixes to said graft sleeve at the first cylindrical wall of the first open end and the second cylindrical wall of the second open end. The polymer material of the graft sleeve includes Polytetrafluoroethylene (PTFE) and the first, second, and third linear connected segments comprise fused portions of the PTFE material. A summation of 1) a circumference of each of the first, second, third and fourth flow channels and 2) twice the sum of the first, second, and third widths of the respective first, second, and third linear connected segments is equal to a circumference of the single tube of polymer material. A first diameter of the first flow channel is within 5% to 25% of the sleeve diameter, a second diameter of the second flow channel is within 5% to 25% of the sleeve diameter, a third diameter of the third flow channel is within 5% to 25% of the sleeve diameter, and a fourth diameter of the fourth flow channel is within 50% to 75% of the sleeve diameter.

The foregoing summary is illustrative only and is not intended to be limiting. Other aspects, features, and advantages of the systems, devices, and methods and/or other subject matter described in this application will become apparent in the teachings set forth below. The summary is provided to introduce a selection of some of the concepts of this disclosure. The summary is not intended to identify key or essential features of any subject matter described herein

BRIEF DESCRIPTION OF THE DRAWINGS

Various examples are depicted in the accompanying drawings for illustrative purposes, and should in no way be interpreted as limiting the scope of the examples. Various features of different disclosed examples can be combined to form additional examples, which are part of this disclosure.

FIG. 4A shows an optional configuration for multiple flow channels including a main channel and three branch channels within the graft portion of the stent-graft;

FIG. 4B shows an optional configuration for multiple flow channels including a main channel and two branch channels within the graft portion of the stent-graft;

FIG. 4C shows an optional configuration for multiple flow channels including a main channel and one branch channels within the graft portion of the stent-graft;

FIG. 4D shows an optional configuration for multiple flow channels including two main channels of equal diameter within the graft portion of the stent-graft;

FIG. 4E shows a side view of the graft portion in FIG. 4A;

FIG. 4F shows a side view of the graft portion in FIG. 4B;

FIG. 4G shows a side view of the graft portion in FIG. 4C;

FIG. 4H shows a side view of the graft portion in FIG. 4D;

FIG. 12 shows alignment of the stent portion with the graft portion;

DETAILED DESCRIPTION

Figure 1A:
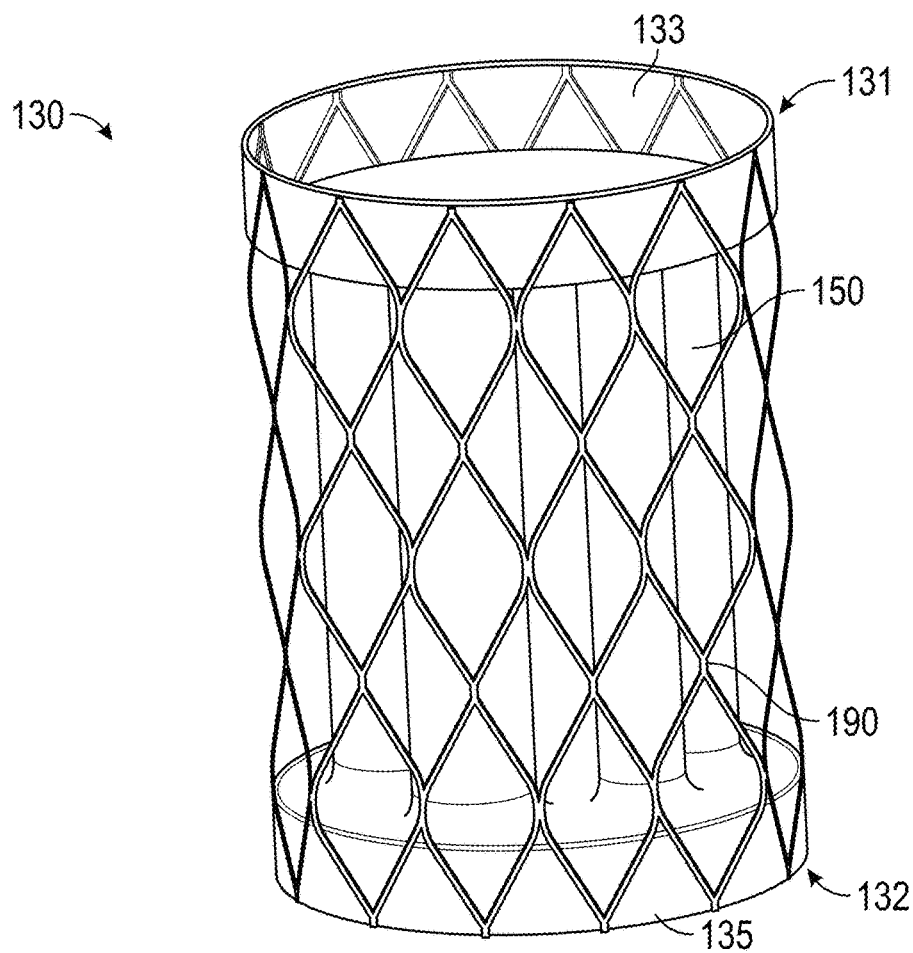
FIG. 1A shows a perspective view of a stent-graft including a stent portion and a graft portion.
Figure 1B:
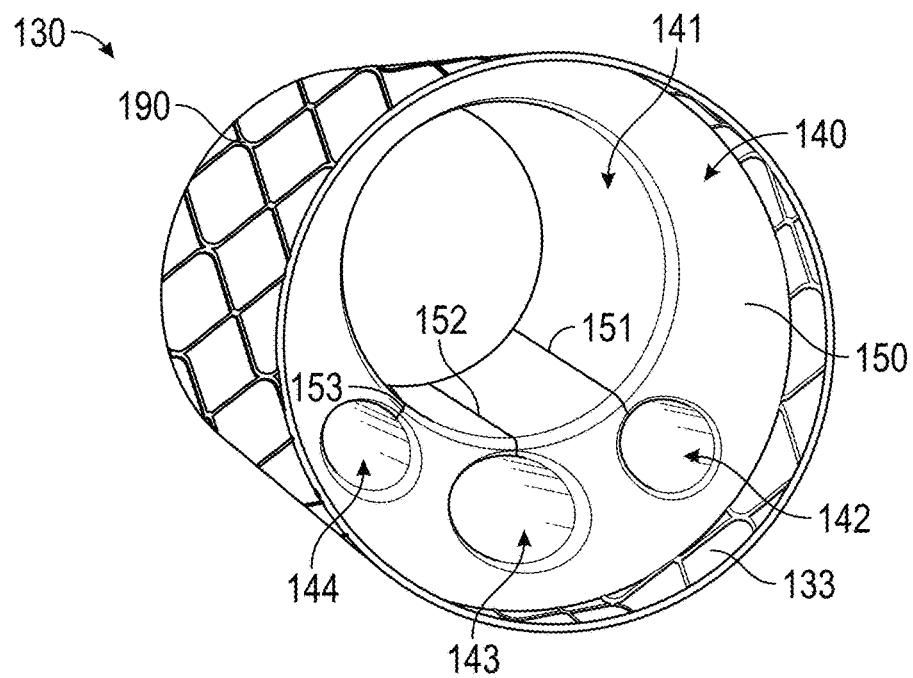
FIG. 1B shows an end perspective view of the stent-graft.
Figure 1C:
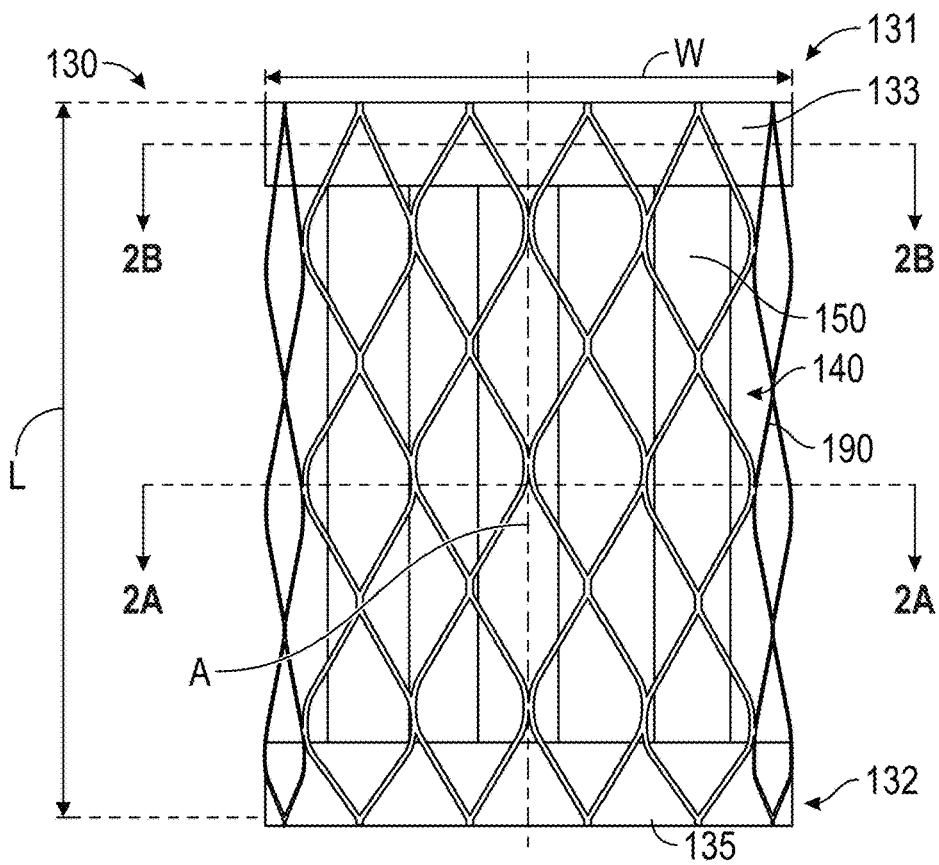
FIG. 1C shows a first side view of the stent-graft.
Figure 1D:
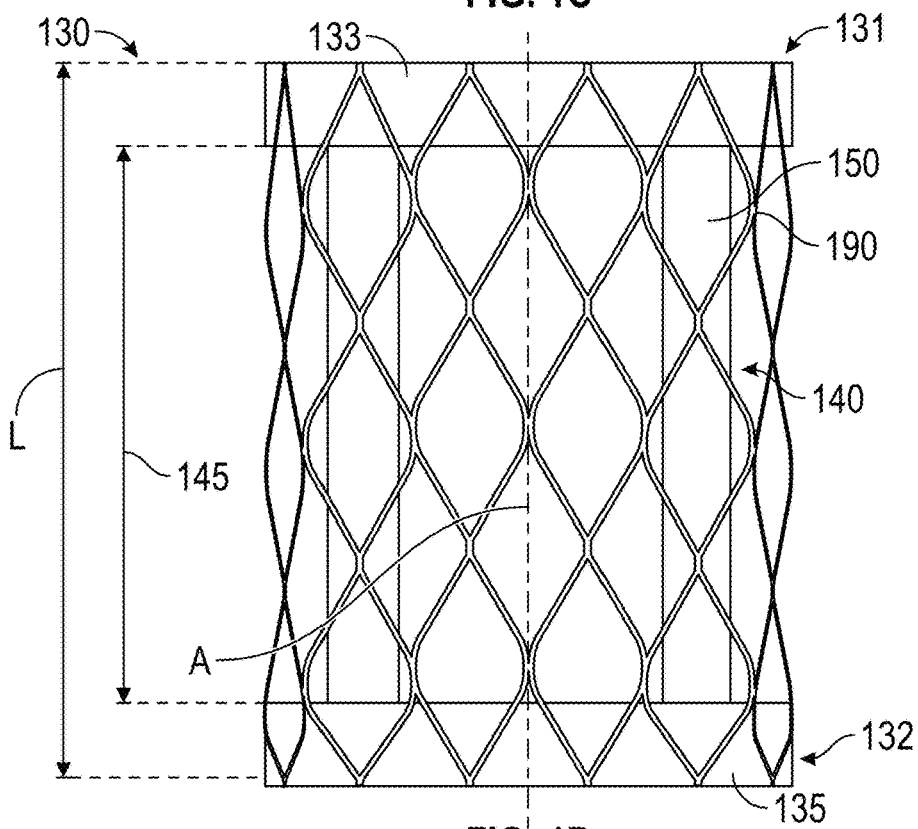
FIG. 1D shows a second side view of the stent-graft.
Figure 1E:
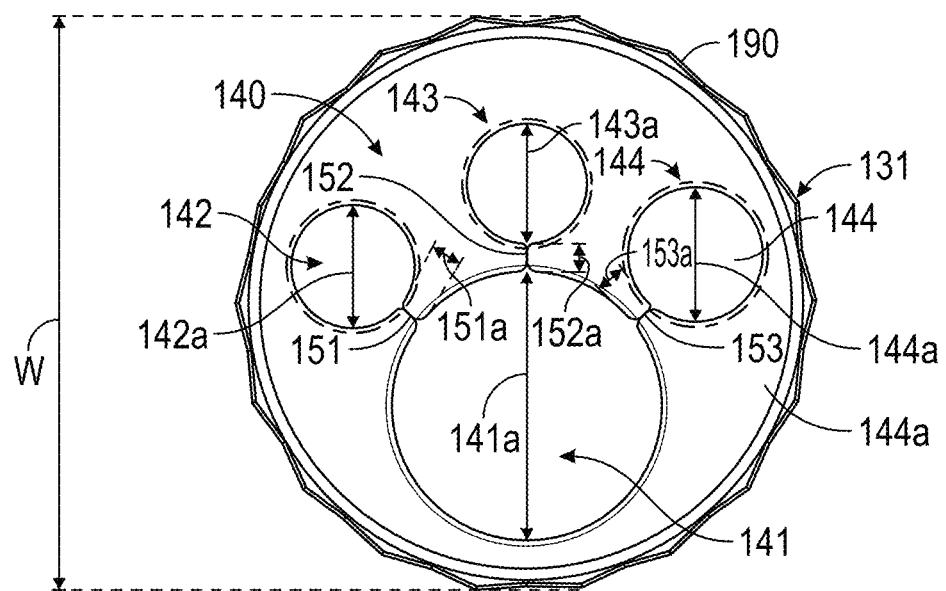
FIG. 1E shows a first end view of the stent-graft.

The various features and advantages of the systems, devices, and methods of the technology described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

Blood vessels may occasionally develop aneurysms, which can rupture and cause fatal hemorrhaging. Accordingly, it has become common practice to bridge damaged vessel segment, such as aneurysm, using a sufficiently long graft secured within the vessel. This bridge can have the effect of reducing hemodynamic forces on the vessel. Depending on the location of the aneurysm, the implantation of the bridging graft can be relatively straight-forward or difficult. Aneurysms that develop within the aortic arch have proven particularly difficult to address for various reasons. One common reason is the sheer number of variations of arterial branching pattern of the aortic arch between people. The aortic arch includes the ascending and descending aorta and typically includes three major arterial branches located in close succession: the brachiocephalic artery (leading to the right subclavian artery and the right common carotid artery), the left common carotid artery, and the left subclavian artery. While this arterial branching pattern is the most common, the spacing and layout between the three branches varies from person to person. Other arterial branching patterns are also fairly common: the left carotid artery can originate from the brachiocephalic artery rather than the aortic arch; the left carotid artery can originate from the aortic arch at the same location as brachiocephalic artery; and the left carotid artery and the left subclavian artery can branch from a common trunk connected with the aorta, etc.

Because of the arterial branching pattern variations and relative inaccessibility of the aortic arch, traditional surgical techniques and apparatus for addressing aneurysms have produced less than satisfactory results. Using conventional techniques, a person's arterial branching pattern would generally require making a custom graft or call for large inventories of fenestrated prosthesis. For example, a fenestrated graft would require placement of windows to align with each the patient's branch vessels. During surgery, each of the branches would need to be connected to the main stent-graft using a connection graft. However, the position of a window with respect to a branch vessel may be misaligned or offset when the stent-graft is deployed. It may also be difficult to deploy guide wires and catheters from the stent-graft into the branch vessel to enable correct positioning of the connection graft. Also, when the window is offset from the branch vessel, the connection graft may kink to such an extent that blood flow will not occur through it.

Accordingly, the present disclosure includes an improved stent-graft hub and prostheses, improved manufacturing processes and improved surgical techniques that address the current inadequacies and provide improved medical outcomes for aortic arch an other types of surgeries.

FIGS. 1A-F show an example of a multi-lumen stent-graft 130 including a graft portion 150 and a stent portion 190. The stent portion 190 can comprise a shape and memory alloy such as super elastic nitinol or similar material. Desirably, the graft portion 150 can be made of a sheet of polytetrafluoroethylene (PTFE). The graft portion 150 can alternatively be made of Dacron, polyester, and/or other synthetic materials known to those of skill in the art. Optionally, the material of the graft portion 150 can be generally non-stretching.

The stent-graft 130 can include a first open end 131 and a second open end 132 opposite the first open end 131. The first end 131 can have a circular shape, although this is not required. The second end 132 can have the same shape as the first end 131, although this is not required. The stent-graft 130 can have a diameter W. The diameter W can be uniform from the first end 131 to the second end 132. In other implementations, the first and second ends 131, 132 can have different diameters. The diameter W can be between approximately 10 mm and 50 mm, depending on the application. In one example, the first end 131 can have a diameter equal to approximately 25 mm. The second end 132 can have the same diameter or a different diameter than the first end 131. The stent-graft 130 can have a hub length L from the first end 131 to the second end 132. The hub length L can extend from an upper rim of the first end 131 to a lower rim of the second end 132. The hub length L can be between approximately 1 cm and 15 cm, depending on the application.

The first end 131 can comprise a cylindrical wall 133. The cylindrical wall 133 can include one or more end portions of the stent portion 190 and/or one or more portions of the graft portion 150. The graft portion 150 can be attached along an inner side and/or outer side of the cylindrical wall 133. The cylindrical wall 133 can include one or more folded portions of the graft portion 150. The graft portion 150 can be attached to itself through openings in the stent portion 190 (e.g., via adhesive, suturing, fusing, or other techniques). The cylindrical wall 133 can be supported by the stent portion 190. The cylindrical walls 133, 135 can have lengths 131a, 132a between approximately 1 mm and 80 mm, depending on the application. A cross-section shown in FIG.

Figure 2A:
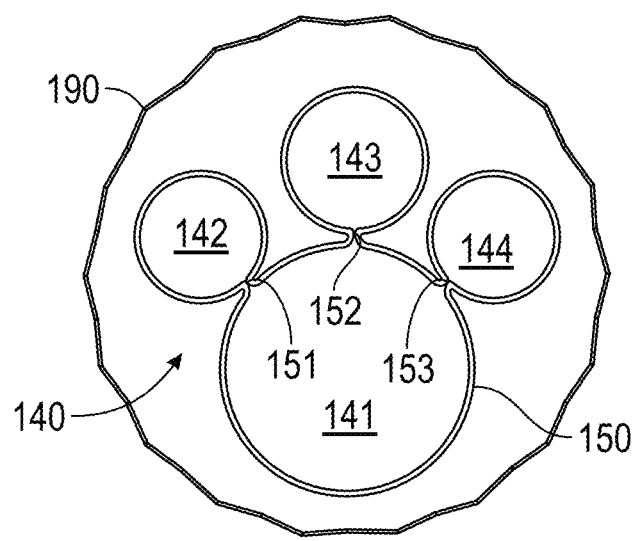
FIG. 2A shows a section view taken at line 2A-2A in FIG. 1C.
Figure 2B:
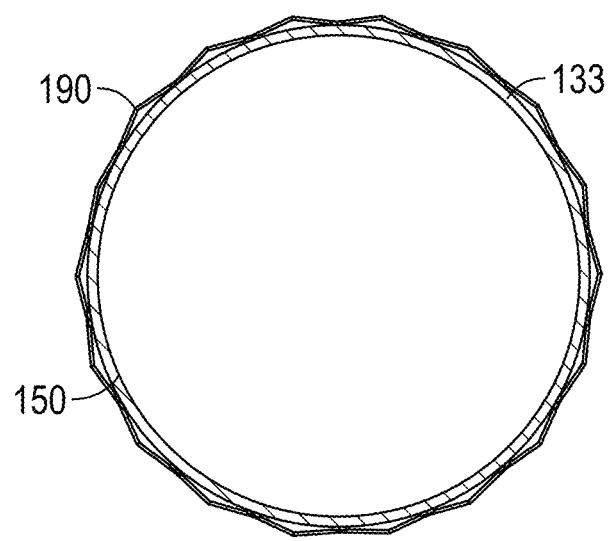
FIG. 2B shows a section view taken at line 2B-2B in FIG. 1C.

2B taken along the line 2B-2B in FIG. 2A extends through the cylindrical wall 133 and shows an inner periphery of the graft portion 150. The inner periphery of the cylindrical wall 133 can have a circular shape having the diameter W. Similarly, the second end 132 can include a cylindrical wall 135 having the same structure as the cylindrical wall 133, although this is not required.

The graft portion 150 can include the plurality of flow channels 140 that extend through the stent-graft 130. The channels 140 can provide fluid flow between the first end 131 and the second end 132. Each of the channels 140 can be sealed from the others of the channels 140. Each of the channels 140 can be formed of the graft portion 150. Each of the channels 140 can include an inlet on one end of the stent-graft 130 and an outlet on an opposite end of the stent-graft 130 (e.g., either on the first end 131 or the second end 132). The cylindrical walls 133, 135 can offset the inlets/outlets of the channels 140 away from terminal rims of the respective first and second end 131, 132. Each of the channels 140 can be parallel with a longitudinal axis A of the stent-graft 130. The channels 140 can be unsupported by the self-expanding wire stent (i.e., between the first and second ends 131, 132).

The channels 140 of the stent-graft 130 can include first, second, third, and fourth channels, 141-144. The stent-graft 130 can include the channels 141-144 for creating a stent-graft hub for use in a prostheses within the aortic arch of a patient and facilitating bridging of an aneurysm and connection of multiple branch arteries extending from the aortic arch with the stent-graft hub. In other examples of stent-grafts more or fewer channels can be included. The number of channels can be based on the application, the planned prosthetic, and/or the location of use (e.g., aortic arch, thoracic aorta, or other).

The diameters of the channels 140 can be uniform between the inlet and the outlet ports of each of the channels. Thus, there can be one diameter that describes each of the channels 140. The first channel 141 can be a main or primary channel having a diameter 141a. The diameter 141a can be greater than the diameters of any or all of the remaining diameters of the channels in the plurality of channels 140. The second channel 142 can have a diameter 142a. The third channel 143 can have a diameter 143a. The fourth channel 144 can have a diameter 144a.

Desirably, the graft portion 150 can be formed of a single sleeve or tube comprising one or more sheets of material (e.g., bonded together). The channels 140 can each be formed of the graft portion 150 along linear connected segments. The linear connected segments can comprise fused lines. The linear connected segments can extend parallel with a longitudinal axis A of the stent-graft 130. The linear connected segments can include material of the graft portion 150 that is connected together (e.g., via suturing, melting/fusing, or adhesives, or other means) along a line. Fused lines can be formed via melting of the graft material such as through heating above a melting temperature thereof or ultrasonic welding. In certain implementations, the graft material of the graft portion 150 can comprise PTFE and the linear connected segments can comprise fused portions of the PTFE. Fused lines can provided a superior connection mechanism relative to suturing or adhesives. By bonding and intermingling of the material of different portions of the graft portion 150, the channels 140 can be formed without the need to introduce additional materials. This streamlines the manufacturing process and reduces the risk of foreign materials being present within the vessels. Alternatively, the graft portion 150 can comprise a woven material such as woven polyethylene terephthalate (DACRON) and the linear connected segments can comprise sutures.

In the present example, the second channel 142 can be separated from the first channel 141 by a linear connected segment 151 in the graft portion 150. In the present example, the third channel 143 can be separated from the first channel 141 by a linear connected segment 152 in the graft portion 150. In the present example, the fourth channel 144 can be separated from the first channel 141 by a linear connected segments 153 in the graft portion 150. Each of the linear connected segments can include a width 151a, 152a, 153a extended between the relevant channel portions 140. In certain implementations, the widths 151a, 152a, 153a can be between 1.0 mm and 2.0 mm, or between 0.5 mm and 5 mm.

Assuming no stretching or folding or overlapping of the graft portion 150 at the first and second ends 131, 132, the circumference of the single tube can be equal to the summation of the circumferences of the channels 140 and twice the lengths of the widths between the channels (e.g., 151a-153a). Assuming the graft portion 150 and the channels 140 are circular and the widths between channels are small, the summation of the circumferences of the channels 140 can be approximately equal to the circumference of the single tube having circumference (e.g.: $\pi*W=\pi(141a+142a+143a+144a\ldots)$).

Figure 1F:
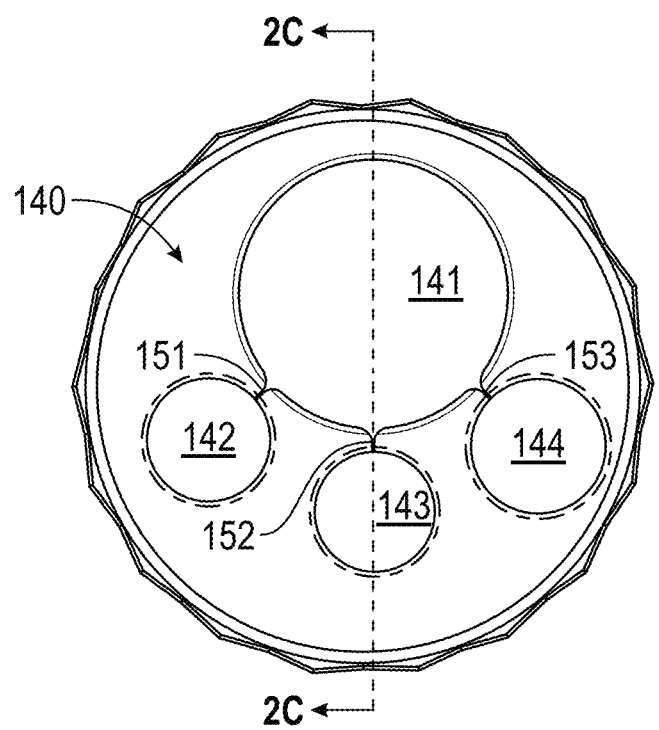
FIG. 1F shows a second end view of the stent-graft.
Figure 2C:
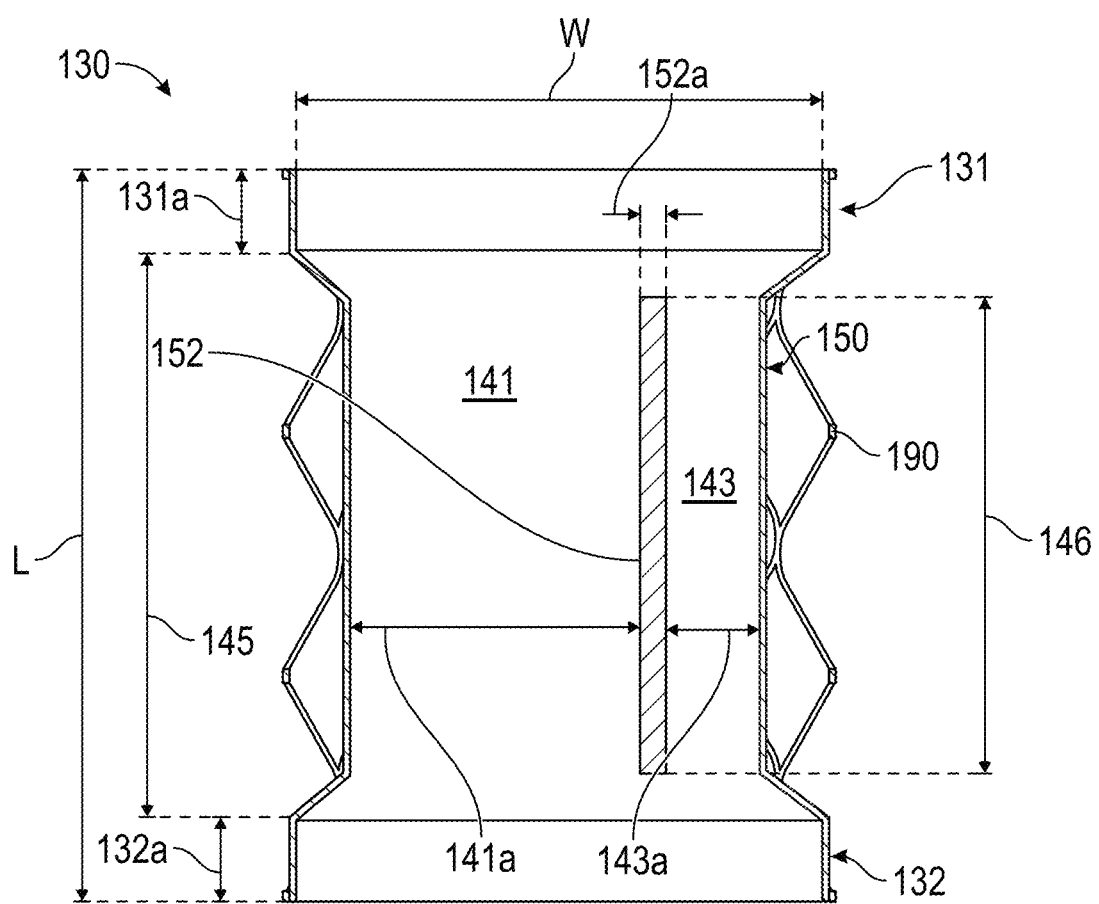
FIG. 2C shows a section view taken at line 2C-2C in FIG. 1F.

FIG. 2C shows a cross-section taken along the line 2C-2C in FIG. 1F extending through the first channel 141 and the third channel 143. The channels 140 can extend from the first open end 131 to the second open end 132 along a channel length 145. The channel length 145 can extend parallel with the longitudinal axis and/or the axes of the channels 141-144 of the channels 140. The channel length 145 can extend from the cylindrical wall 133 to the cylindrical wall 135 (e.g., the base of the cylindrical walls). Desirably, the channel length 145 can be approximately 75% or between 50% and 90% of the hub length L. This arrangement can provide a compact arrangement for the multi-lumen stent-graft 130. While longer stent-grafts can too difficult to deploy and/or too difficult to connect with connecting stents, as described below, the compact arrangement of the stent-graft 130 can provide for use within tight, crowded environments, such as the aortic arch. The compact arrangement, together with a low hub length L (e.g., between 4 and 9 cm), can provide for placement of the multi-lumen stent-graft 130 within multiple different positions within the aortic arch (e.g., either ascending or descending aorta). The ratio of the channel length 145 to the overall length L within the high ranges provided herein and shown in FIG. 2C can also provide for sufficient length (and surface area) of the channel 140 to securely engage with the connecting stents, as described below. The total surface area overlap between the connecting stents and the channels can be directly proportional to the strength of the connection between the connecting stents and the stent-graft 130. In other arrangements, the channel length 145 can be 75% and 90% or between 50% and 95% of the hub length L. Each of the channels 140 can extend the channel length 145 (e.g., the channels 140 can have the same length). The channels 140 can also extend along a seal length 146. The seal length 146 can extend parallel with the longitudinal axis and/or the axes of the channels 141-144 of the channels 140. The seal length 146 can extend from an upper end to a lower end of any of the linear connected segments 151-153. Desirably, the seal length 146 can be between 75% and 100% of the channel length 145. This arrangement can provide a compact structure of the multi-lumen stent-graft 130. In other arrangements, seal length 146 can be 75% and 90% or between 50% and 95% of the hub length L.

Figure 3A:
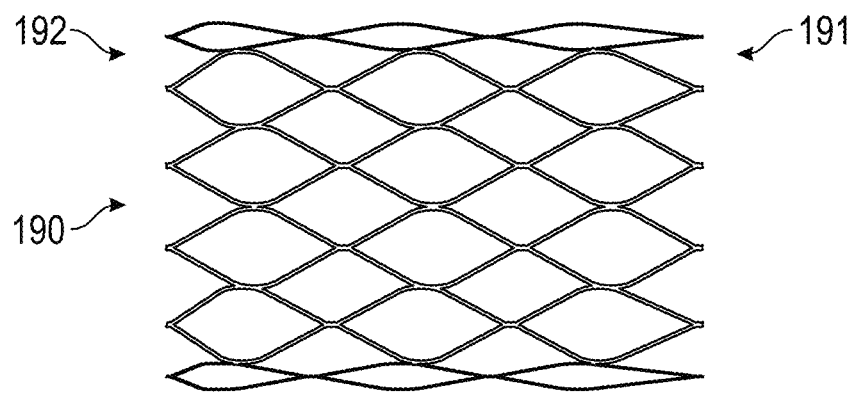
FIG. 3A shows a side view of the stent portion of the stent-graft.
Figure 3B:
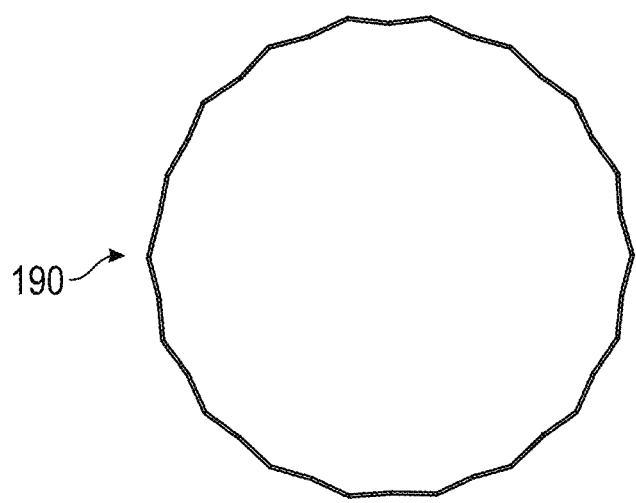
FIG. 3B shows an end view of the stent portion of the stent-graft.

FIGS. 3A-B show the stent portion 190 separated from the graft portion 150. The stent portion 190 can comprise a self-expanding wire structure that can be collapsed so as to be insertable via a catheter into a body vessel such as artery or vein. The material of the stent portion 190 can include nitinol and other similar (e.g., bio-inert) materials such materials. The stent portion 190 can comprise a plurality of wires formed in a honeycomb or cross pattern according to conventional structures that are known for the construction of wire stents. The stent portion 190 can include a first end 191 and a second end 192. The stent portion 190 can be formed generally as a cylinder with a central passageway extending therethrough. The first end 131 can terminate in a plurality of joints and intersections of the wires forming the stent portion 190. The stent portion 190 can be coaxially mounted on the graft portion 150. The stent portion 190 can be connected with the graft portion 150 using sutures or other mechanical fasteners. The stent portion 190 can include wires formed in a diamond-shaped overlap pattern.

In certain implementations the wires can comprise barbs or other projections that can be used to attach more securely with other stent-grafts or portions of the vessel wall. The barbs can be extensions of a stent portion 190. The barbs can extend longitudinally outwardly and/or radially outwardly or inwardly of the first and/or second ends 131, 132. The barbs can provide connection points with an interior portion of a human vessel (e.g., oriented outwardly) and/or connection points with connecting grafts that can be attached within the stent-graft 130 (e.g., oriented inwardly). Radiopaque materials and/or marks can also be included on the stent-graft 130, such as attached with the graft portion 150 or on the stent portion 190.

FIGS. 4A-H show the graft portion 150 without the stent portion 190 and having various arrangements 140a-d for the channels 140 extending therethrough. The channels 140 can include two, three, four, five, six, or more channels. The channels 140 can be formed using linear connected segments in the graft portion 150 formed of a single tube. The stent-grafts 130 having various numbers and arrangements of the channels 140. In one implementations, a set of stent-grafts can be compiled from which one or more stent-grafts can be selected for use during surgery. The selection from the set can be based on the intended use of the particular stent-graft 130 (e.g., the arterial branching pattern of a patient). Advantageously, the set reduces the need for custom-made components or carrying large stocks of physiologically specific components.

The relative diameters of the channels 140a-d relative to the width W can be based on the number of channels. In certain examples, the channel diameters can be according to the following chart:

| Number of Channels | Main Channel (% of W) | Branch channels (% of W) |
|---|---|---|
| 2 | 50-80 | 20-50 |
| 3 | 50-80 | 10-40 |
| 4 | 50-75 | 5-25 |
| 5+ | 50-65 | 5-20 |

Figure 5:
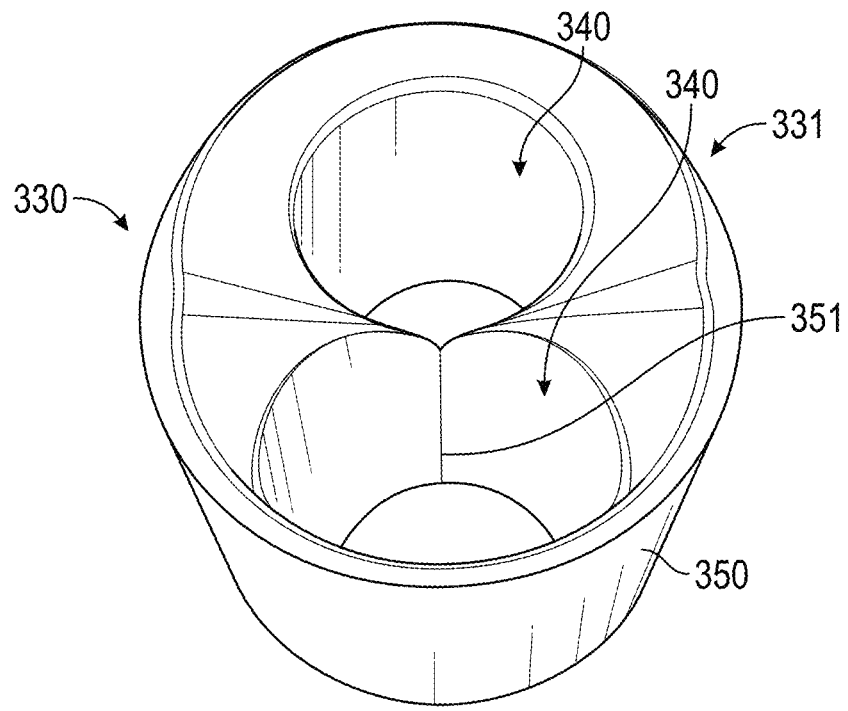
FIG. 5 shows a front perspective view of another example of a stent-graft.
Figure 6:
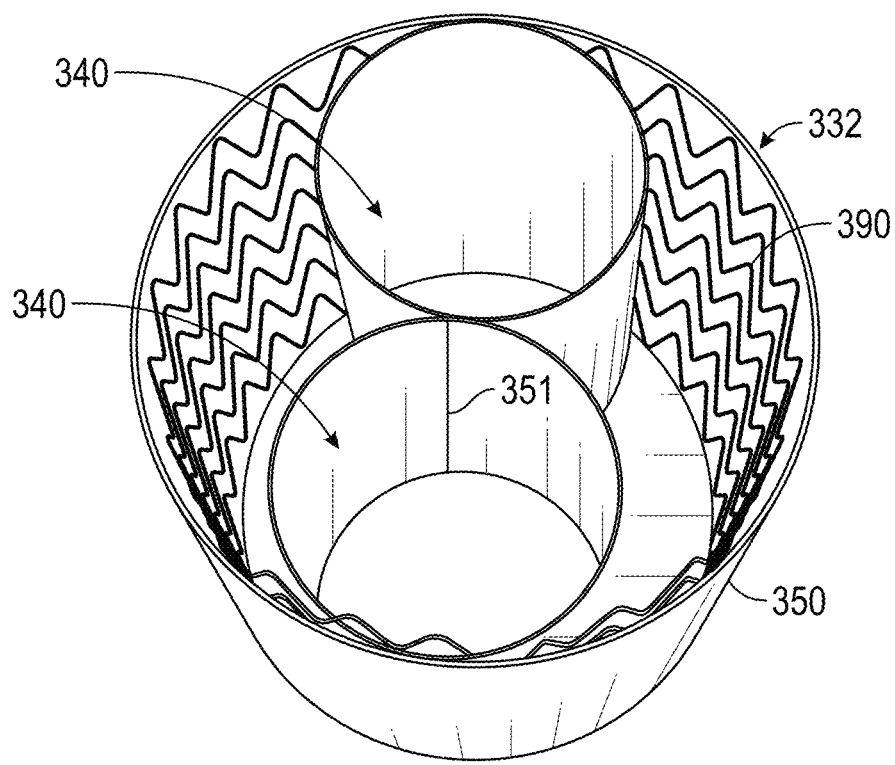
FIG. 6 shows a rear perspective view of the stent-graft of FIG. 5.
Figure 7:
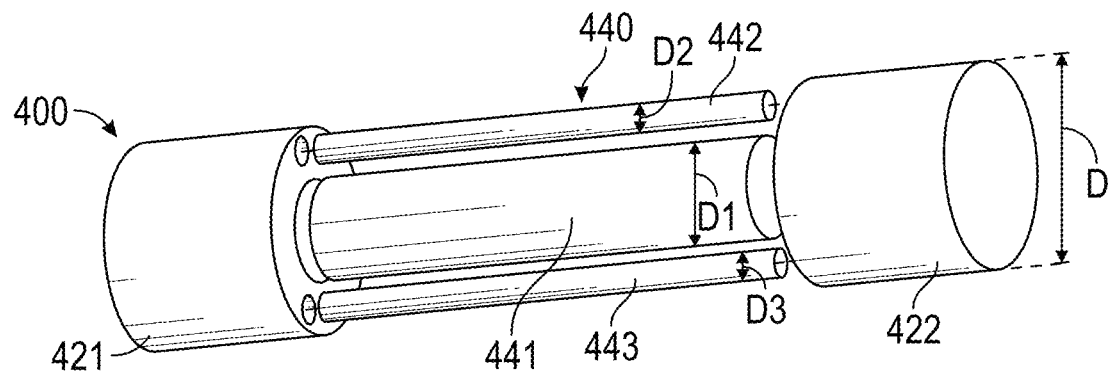
FIG. 7 shows an exploded view of a mandrel assembly used in the assembly and manufacture of a stent-graft.

FIGS. 5-6 show another implementation of a stent-graft 330 including a graft portion 350 and a stent portion 390. The stent-graft 330 can include a first end 331 and a second end 332. The first end 331 can be enclosed with the graft portion 350 folded outwardly over an end of the stent portion 390. The graft portion 350 can include channels 340 with inlets that open to the first end 331. The second end 332 can be open between the graft portion 350 and the stent portion 390. As shown in FIG. 6, the graft portion 350 can be assembled over an outer surface of the stent portion 390. The first end 331 includes closed end of the graft portion 350 while the second end 332 includes openings between the channels 340 and the stent portion 390. The outlets of the channels 340 are not directly connected to the graft portion 350 and/or the stent portion 390, but are instead "floating." Advantageously, this allowed increased movement of the channels 340 relative to the stent portion 390 and/or vessel walls.

Figure 8:
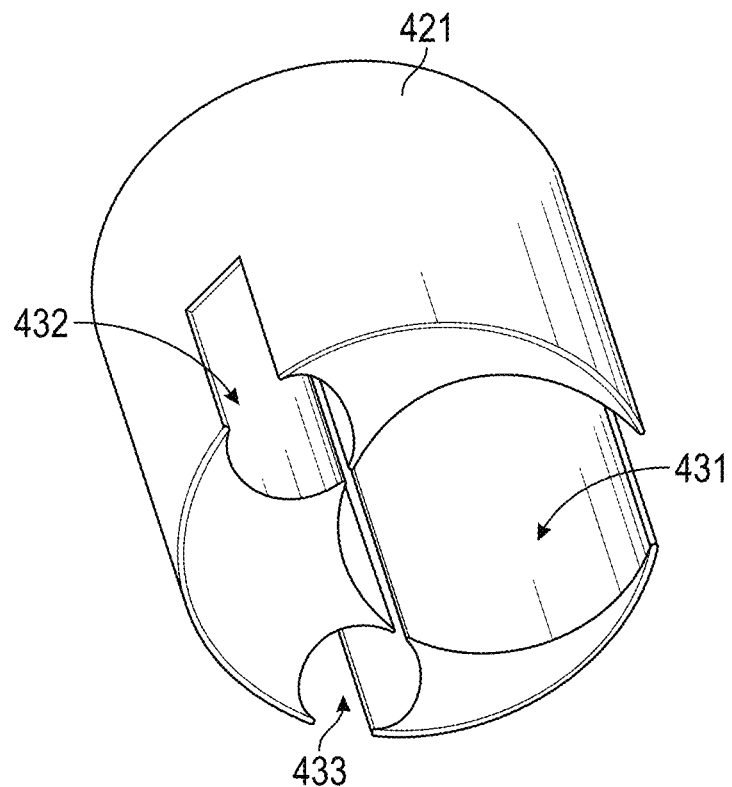
FIG. 8 shows a perspective view of an end cap of the mandrel assembly.

FIGS. 7-14 illustrate an apparatus and method for manufacturing a stent-graft like the stent-graft 130 described above. The apparatus can include a mandrel assembly 400. The mandrel assembly 400 can include end caps 421, 422 and a plurality of channel mandrels 440. The channel mandrels 440 can include any number of members, such as members 441, 442, 443, depending on the desired arrangement for a finished stent-graft 130. The end cap 421 can include a plurality of receptacles therein. The receptacles can include cylindrical-shaped apertures, such as apertures 431, 432, 433. The cylindrical-shaped apertures can be sized to receive one end of each of a plurality of channel mandrels 440. The end cap 421 can be a mirror image of the end cap 422. The cylindrical-shaped apertures of the end cap 422 can receive an opposite end of each of the plurality of channel mandrels 440. The arrangement of the cylindrical-shaped apertures can be selected according to the desired arrangement of the flow channels 140 for a finished stent-graft 130. Optionally, the cylindrical apertures can be connected by one or more slits within the end caps 421, 422, as shown in FIG. 8.

The end caps 421, 422 can have a generally cylindrical body having a diameter D. The diameter D can be equivalent to the diameter W of the stent-graft 130. The channel mandrels 440 can each include a cylindrical body with a diameter, such as diameters D1, D2, D3. The diameters D1-D3 can correspond to the desired diameters of the flow channels 140 of a finished stent-graft 130.

Figure 9:
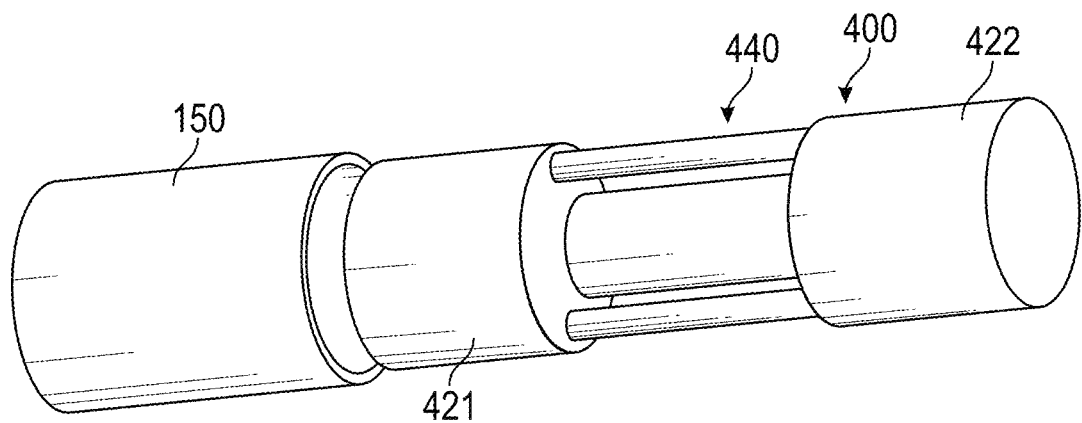
FIG. 9 shows assembly of a tubular graft portion over the mandrel.

The channel mandrels 440 can be assembled within respective apertures of the end caps 421, 422, as shown in FIG. 9. A tubular graft portion 150 can be assembled over the assembled mandrel. Opposite ends of the graft portion 150 can be aligned over the end caps 421, 422. A central portion of the graft portion 150 can be aligned with the channel mandrels 440.

Figure 10:
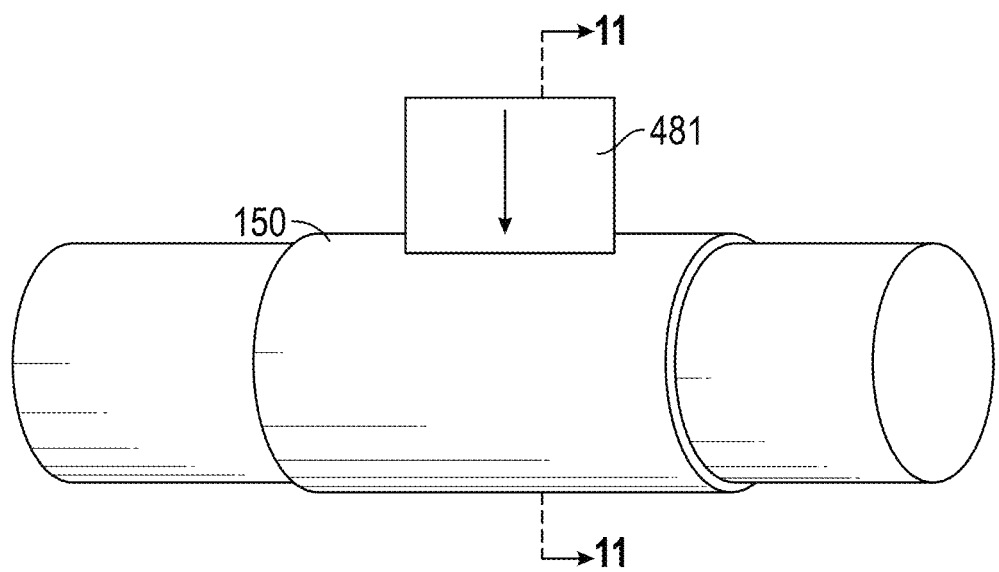
FIG. 10 shows formation of individual flow channels within the stent portion of the stent-graft formed by melting portions of the material of the graft portion between adjacent channel mandrels in the mandrel assembly.
Figure 11:
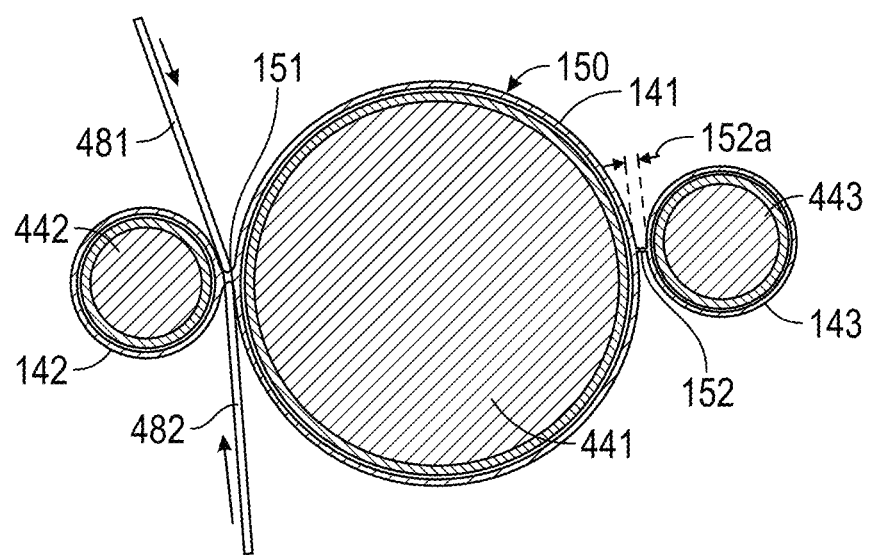
FIG. 11 shows a section view taken along the line 11-11 in FIG. 10.

As shown in FIGS. 10-11, the material of the graft portion 150 can be pushed into contact with itself around the channel mandrels 440 of the mandrel assembly 400 (e.g., members 441, 442, 443, etc.). The contacting portions of the graft portion 150 can be connected together to form the linear connected segments (e.g., segments 151, 152, 153, etc.) that define the channels 140 of the hub 130. As shown in FIG. 11 on the right, the material of the graft portion 150 has been wrapped closely around the member 443 and sealed to itself at the linear connected segment 152 to form the flow channel 143. As shown in FIG. 11 on the left, the material of the graft portion 150 has been wrapped closely around the member 442 and sealed to itself at the linear connected segment 151 to form the flow channel 142. As shown in FIG. 11 at center, the material of the graft portion 150 has been wrapped closely around the member 441 and sealed to itself at the linear connected segments 151 and 152 to form the flow channel 141.

The linear connected segments can define (alone or in combination) the flow channels 140 of the stent-graft 130. The linear connected segments can each comprise a fused line of the material of the graft portion 150. The pattern of the fused line can be a varied. In certain examples, the pattern of the fused line can be continuous or intermittent. In certain examples, the pattern of the fused line can be straight, comprise multiple straight lines (e.g., zig-zag) or curved (e.g., sinusoidal). In certain examples, another material can be included in one or more of the linear connected segments. The additional material can include an intermediate layer of PTFE, fluorinated ethylene propylene (FEP), or other material. The additional material can be placed between the contacting portions of the graft portion 150.

The fusing can be accomplished using a heated iron 481 and/or a second iron 482 or other backing material. The iron 481 can be inserted between adjacent members of the channel mandrels 440, as necessary. Alternatively, the linear connected segments can be sutured, adhered or otherwise connected. Alternatively the fused lines can be formed using ultrasonic welding with an ultrasonic welding tip.

The process can be repeated until all flow channels 140 have been formed. In certain implementations, the graft portion 150 can be formed into the flow channels 140 by starting with the smaller diameter members 440. After completing the smaller flow channel, the largest (primary) flow channel may be completed. The largest diameter member 441 can form the primary flow channel 141, having the largest diameter.

Figure 13:
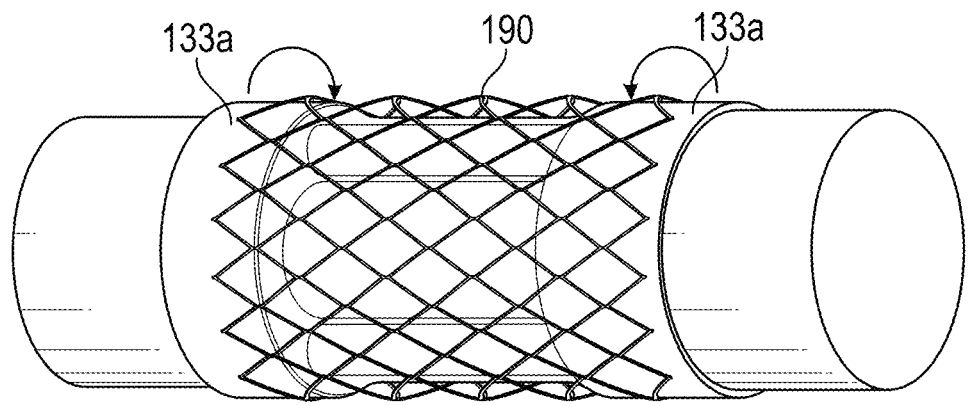
FIG. 13 shows folding of the graft portion over the open ends of the stent portion assembled over the graft portion.
Figure 14:
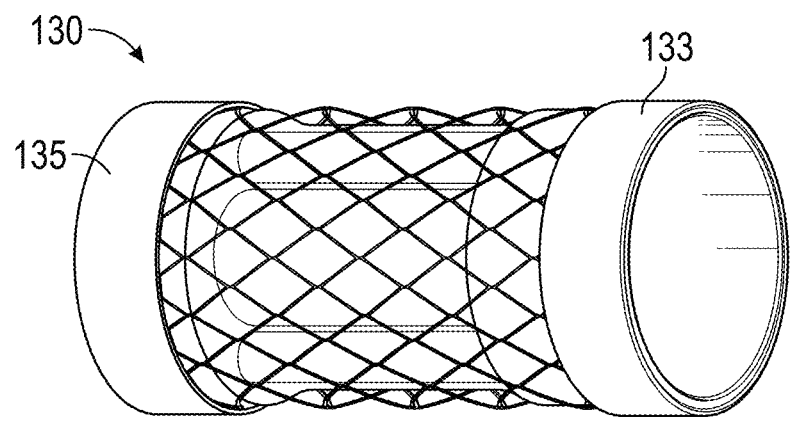
FIG. 14 shows the finished stent-graft.
Figure 15:
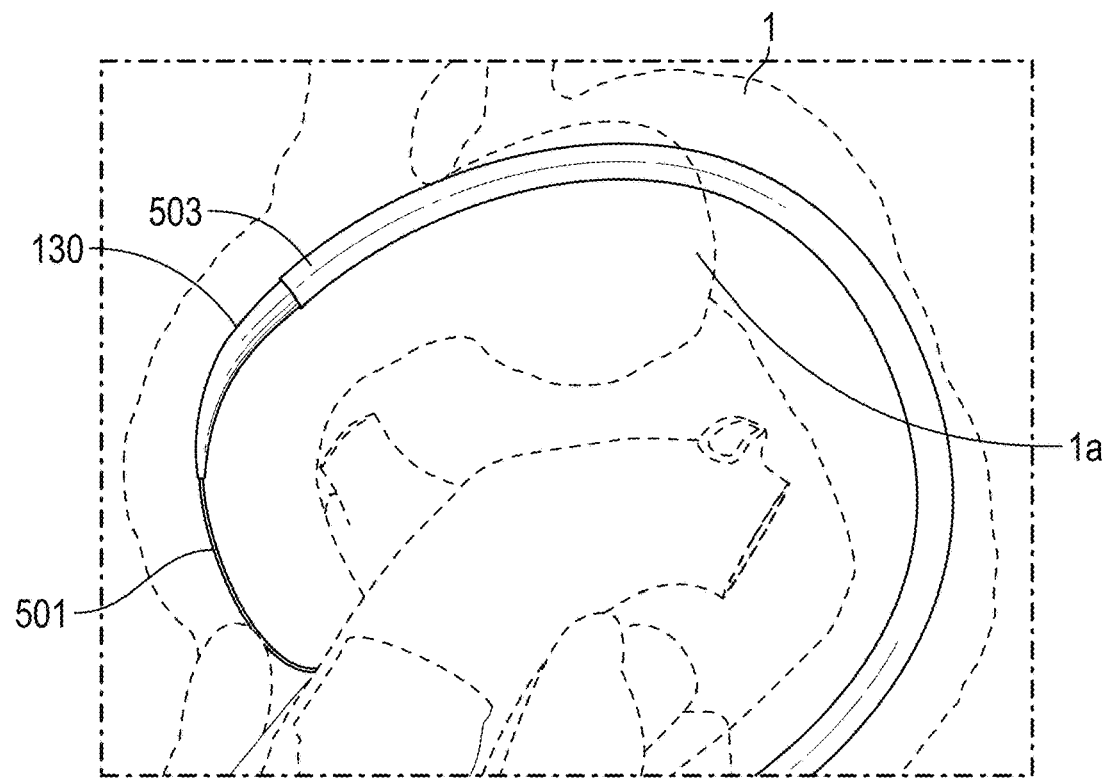
FIG. 15 shows insertion of a catheter into an aorta to bridge an aortic aneurysm.
Figure 16:
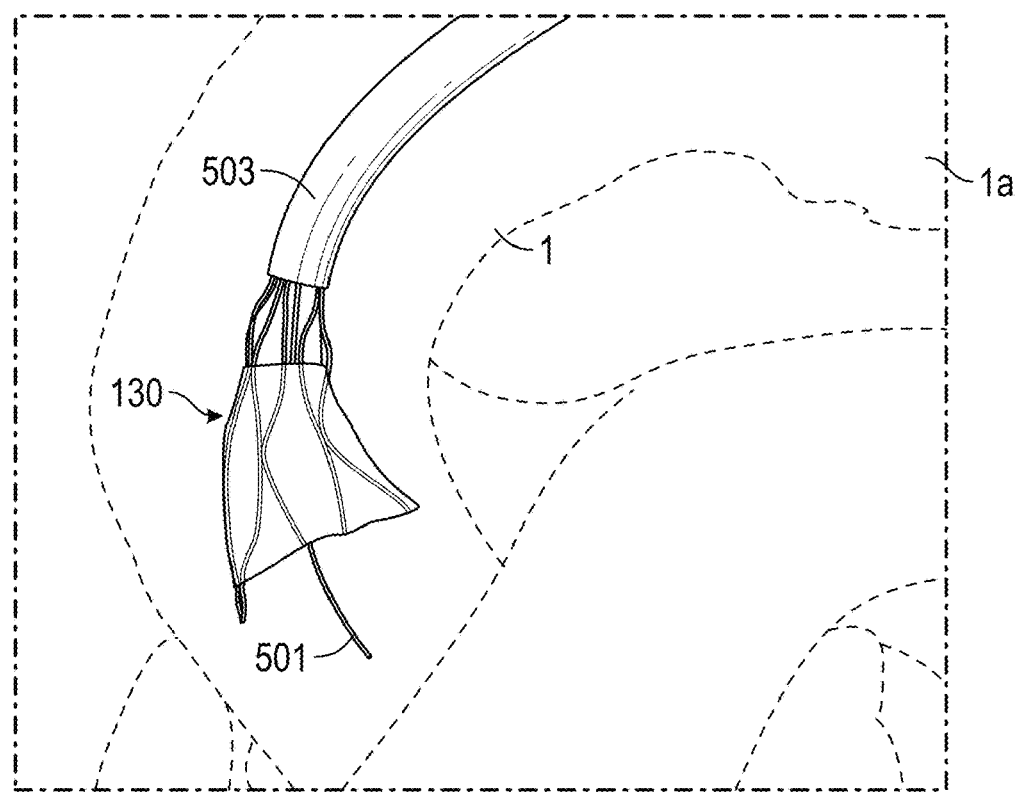
FIG. 16 shows deployment of a stent-graft hub from the catheter within the aorta.

After forming the flow channels 140, the stent portion 190 can be assembled coaxially over the graft portion 150 while still on the mandrel assembly 400, as shown in FIGS. 12-14. The stent portion 190 can be positioned over the flow channels 140. Either end of the stent portion 190 can overlap unfolded ends 133a, 135a of the graft portion 150. After positioning, the unfolded ends 133a, 135a can be sequentially or simultaneously folded over the ends of the stent portion 190 and secured in place (e.g., via suturing, fusing, adhesives, or other). For example, the ends 133a and/or 135a can be melted to encapsulate the ends of the stent portion 190. As an alternative to folding the ends of the graft portion 150, an additional sheet or sheets of PTFE or other material can be positioned over the stent portion 190. The additional material and the ends 133a and/or 135a can sandwich the ends of the stent portion 190. The additional material can then be fused with the ends 133a and/or 135a of the graft portion 150. In certain embodiments, the additional material can fully encapsulate the stent portion 150.

Any additional finishing steps can be completed and the finished stent-graft 130 can be removed by disassembly of the mandrel assembly 400.

FIGS. 15-19 show an example surgical method for placement of a prostheses including a stent-graft 130 into an aortic arch 1 to bridge an aneurysm 1a. Although described in the context of an aortic aneurysm, the techniques discussed herein can be used to address various types of treatment sites (e.g., thoracic aorta). Because of the placement of the aneurysm within the aortic arch, it is likely necessary to bridge to more than one of the branch arteries in the aortic arch. As discussed above, rather than rely on a custom stent-graft, a prostheses can be placed using one or more stent-grafts 130 in conjunction with one or more connecting stent-grafts (e.g., connecting stent graft 522, 523, 524, 525). Each of the connecting stent-grafts can be generally formed as a tube of graft material with or without a self-expanding stent. The diameters and lengths of the connecting stent-grafts can be selected based on the planned placement within the prostheses. For example, the ends of the connecting stent grafts may have different diameters to better fit within channels or branch arteries.

Although the number of stent-grafts 130 used, the number of flow channels 140 in the stent-grafts 130, and the length of the connecting stent-grafts 522-525 can vary, these can be selected from finite set of stent-grafts. This can facilitate and streamline planning and execution of a surgical procedure for a wide variety of prostheses. Although a particular layout of a prostheses is described below, the features of the stent-graft hub 130 and the connecting stents can be adapted to any arterial branching pattern without requiring custom-made components.

A steerable catheter and/or guide wire 501 can be advanced into the aortic arch 1. The guide wire can be inserted through an incision that provides access into the femoral artery and then advanced upwardly into the aortic arch. The guide wire 501 can be advanced in relation to the aneurysms 1a (e.g., above the aneurysm 1a into the ascending aorta). A catheter 503 carrying a collapsed stent-graft 130 can be advanced along the guide wire 501. The collapsed stent-graft 130 can be positioned relative to the aneurysm 1a and deployed using the catheter 503. The stent-graft 130 can be held in-place by radial expansion of the stent-portion 190 and/or through hooks and barbs within an inner wall of the aortic arch 1.

Figure 17:
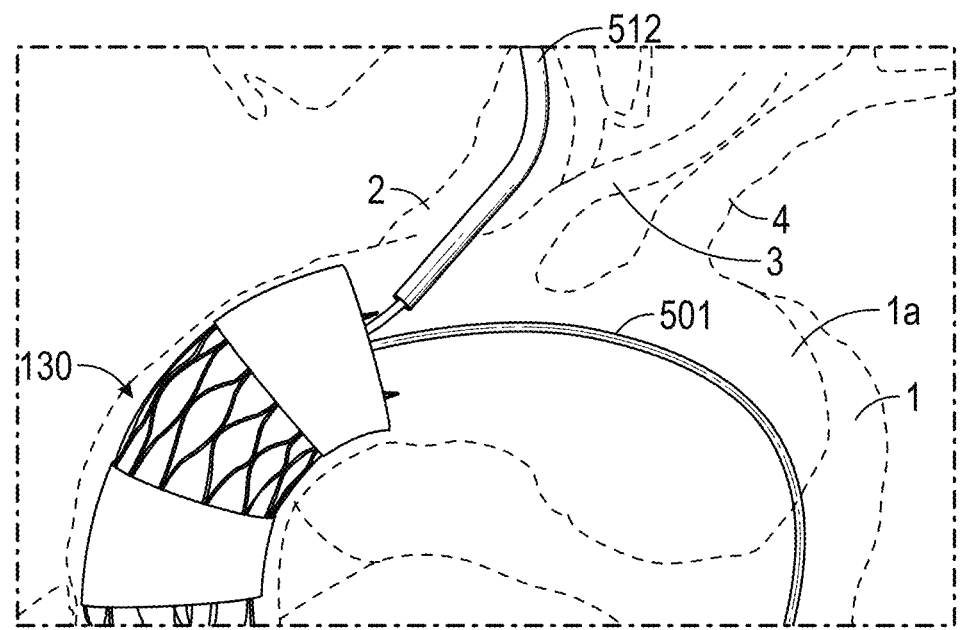
FIG. 17 shows insertion of a first connecting stent-graft from a first branch artery to within a channel of the stent-graft hub.
Figure 18:
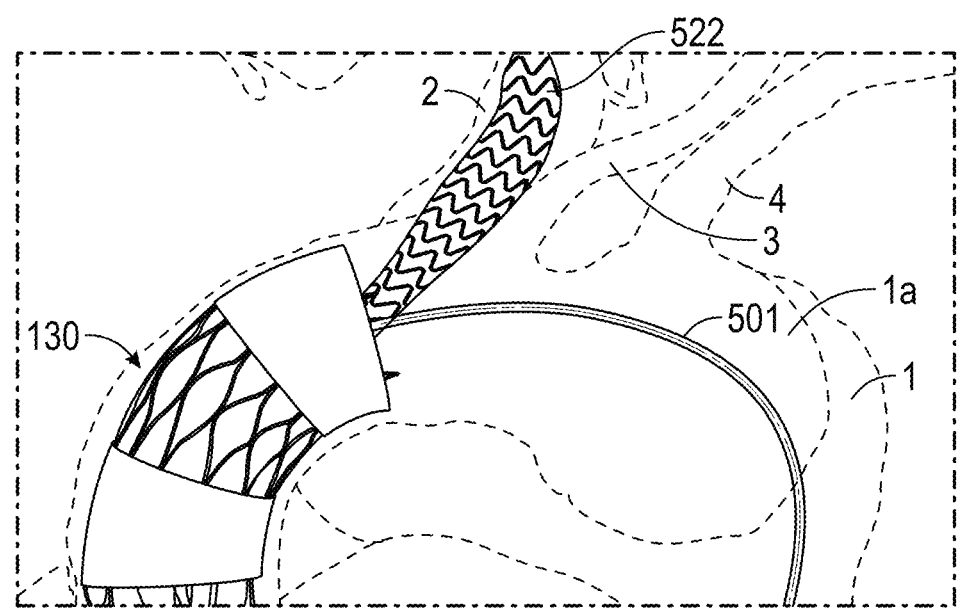
FIG. 18 shows deployment of the first connecting stent-graft within the channel of the stent-graft hub.
Figure 19:
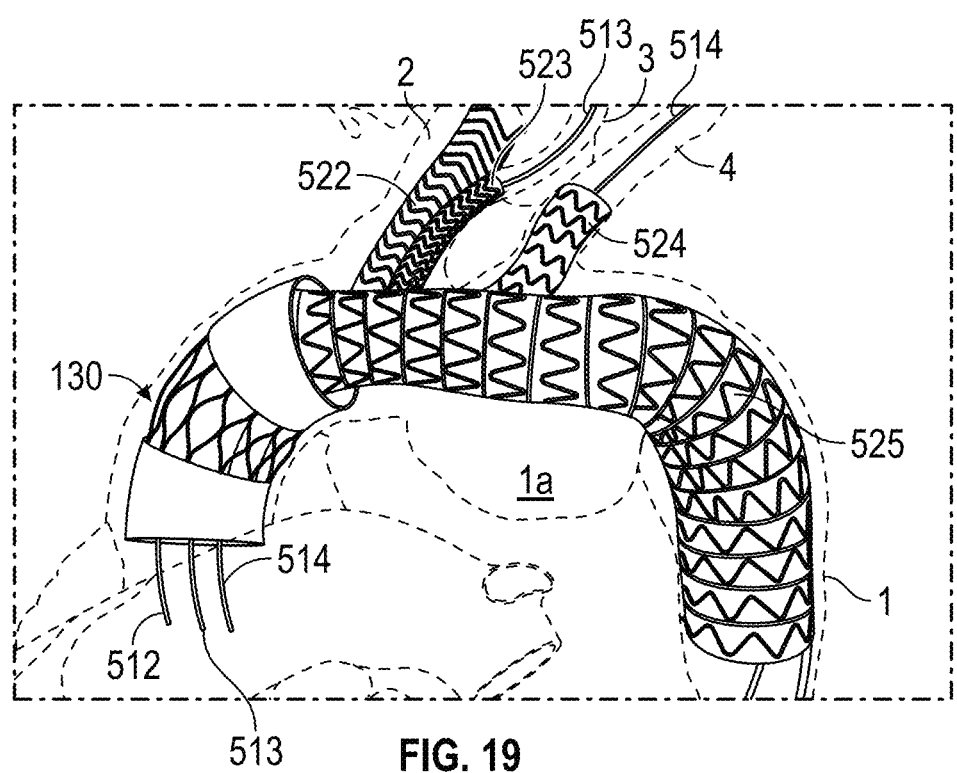
FIG. 19 shows deployment of a prostheses within the aorta to bridge the aortic aneurysm including multiple connecting stent-graft coupled within the stent-graft hub.

As shown in FIG. 17, a guide wire and/or a catheter 512 can be advanced through the brachiocephalic artery 2 (via either the right subclavian artery or the right common carotid artery) and into one of the channels 140 of the stent-graft 130. A connecting stent-graft 522 can be deployed by the catheter 512. A first end of the connecting stent-graft 522 can be disposed within the channel 140 of the stent-graft 130. A second end of the connecting stent-graft 522 can be disposed within the brachiocephalic artery 2. The connecting stent-graft 522 can be deployed from the catheter 512 and radially expanded within the channel 140 of the stent-graft 130. The connecting stent-graft 522 can be held in-place by radial expansion of the stent-portion thereof and/or through hooks and barbs within in an inner wall of the channel 140. The connecting stent-graft 522 can thereby provide a fluid flow path for blood flow between the stent-graft 130 and the brachiocephalic artery 2.

Another guide wire and/or a catheter 513 can be advanced through the left common carotid artery 3 and into another one of the channels 140 of the stent-graft 130. A connecting stent-graft 523 can be deployed by the catheter. A first end of the connecting stent-graft 523 can be disposed within the channel 140 of the stent-graft 130. A second end of the connecting stent-graft 523 can be disposed within the left common carotid artery 3. The connecting stent-graft 523 can be deployed from the catheter 513 and radially expanded within the channel 140 of the stent-graft 130. The connecting stent-graft 523 can be held in-place by radial expansion of the stent-portion thereof and/or through hooks and barbs within in an inner wall of the channel 140. The connecting stent-graft 523 can thereby provide a fluid flow path for blood flow between the stent-graft 130 and the left common carotid artery 3.

Another guide wire and/or a catheter 514 can be advanced through the left subclavian artery 4 and into another one of the channels 140 of the stent-graft 130. A connecting stent-graft 524 can be deployed by the catheter. A first end of the connecting stent-graft 524 can be disposed within the channel 140 of the stent-graft 130. A second end of the connecting stent-graft 524 can be disposed within the left subclavian artery 4. The connecting stent-graft 524 can be deployed from the catheter 514 and radially expanded within the channel 140 of the stent-graft 130. The connecting stent-graft 524 can be held in-place by radial expansion of the stent-portion thereof and/or through hooks and barbs within in an inner wall of the channel 140. The connecting stent-graft 524 can thereby provide a fluid flow path for blood flow between the stent-graft 130 and the left subclavian artery 4. Alternatively, the second end of the connecting stent-graft 524 can be disposed within the aorta 1, such as below the stent-graft 130 or within the descending aorta.

Another guide wire and/or a catheter, such as the guide wire 501, can be advanced within the aortic arch and into another one of the channels 140 of the stent-graft 130, such as the primary flow channel. Another connecting stent-graft 525 can be deployed by the catheter. A first end of the connecting stent-graft 525 can be disposed within the channel 140 of the stent-graft 130 (such as the primary channel 141). A second end of the connecting stent-graft 525 can be disposed within aorta, such as within the aortic arch. The connecting stent-graft 525 can be deployed from the catheter and radially expanded within the channel 140 of the stent-graft 130. The connecting stent-graft 525 can be held in-place by radial expansion of the stent-portion thereof and/or through hooks and barbs within in an inner wall of the channel 140. The connecting stent-graft 525 can thereby provide a fluid flow path for blood flow between the stent-graft 130 and the aorta and bridge the aneurysm 1a.

Figure 20:
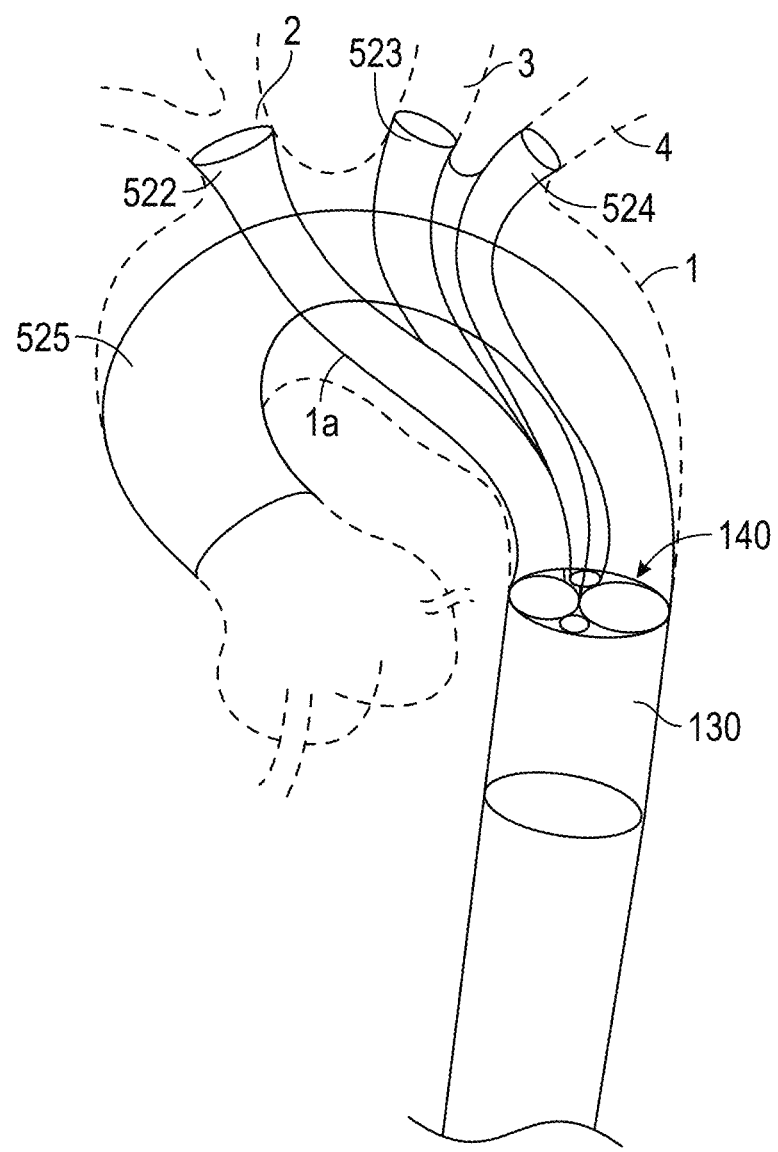
FIG. 20 shows an alternative prostheses.

FIG. 20 shows another example prostheses including a stent-graft 130 within an aortic arch 1 for bridging an aneurysm 1a. A guide wire can be advanced in relation to the aneurysms 1a. A catheter carrying a collapsed stent-graft 130 can be advanced along the guide wire. The collapsed stent-graft 130 can be positioned relative to the aneurysm 1a and deployed using the catheter (e.g., below the aneurysm 1a into the descending aorta).

A guide wire and/or a catheter can be advanced through the brachiocephalic artery 2 (e.g., via either the right subclavian artery or the right common carotid artery) and into one of the channels 140 of the stent-graft 130. A connecting stent-graft 522 can be deployed by the catheter 512. A first end of the connecting stent-graft 522 can be disposed within the channel 140 of the stent-graft 130. The first end of the connecting stent-graft can be deployed and radially expanded within the channel 140. A second end of the connecting stent-graft 522 can be disposed within the brachiocephalic artery 2. The connecting stent-graft 522 can thereby provide a fluid flow path for blood flow between the stent-graft 130 and the brachiocephalic artery 2.

Another guide wire and/or a catheter can be advanced through the left common carotid artery 3 and into another one of the channels 140 of the stent-graft 130. A connecting stent-graft 523 can be deployed by the catheter. A first end of the connecting stent-graft 523 can be disposed within the channel 140 of the stent-graft 130. The first end of the connecting stent-graft can be deployed and radially expanded within the channel 140. A second end of the connecting stent-graft 523 can be disposed within the left common carotid artery 3. The connecting stent-graft 523 can thereby provide a fluid flow path for blood flow between the stent-graft 130 and the left common carotid artery 3.

Another guide wire and/or a catheter can be advanced through the left subclavian artery 4 and into another one of the channels 140 of the stent-graft 130. A connecting stent-graft 524 can be deployed by the catheter. A first end of the connecting stent-graft 524 can be disposed within the channel 140 of the stent-graft 130. The first end of the connecting stent-graft can be deployed and radially expanded within the channel 140. A second end of the connecting stent-graft 524 can be disposed within the left subclavian artery 4. The connecting stent-graft 524 can thereby provide a fluid flow path for blood flow between the stent-graft 130 and the left subclavian artery 4.

Another guide wire and/or a catheter can be advanced within the aortic arch and through another one of the channels 140 of the stent-graft 130, such as the primary flow channel. Another connecting stent-graft 525 can be deployed by the catheter. A first end of the connecting stent-graft 525 can be disposed within aorta, such as within the aortic arch. A second end of the connecting stent-graft 525 can be disposed within the channel 140 of the stent-graft 130. The second end of the connecting stent-graft can be deployed and radially expanded within the channel 140. The connecting stent-graft 525 can thereby provide a fluid flow path for blood flow between the stent-graft 130 and the aorta and bridge the aneurysm 1a.

Figure 21:
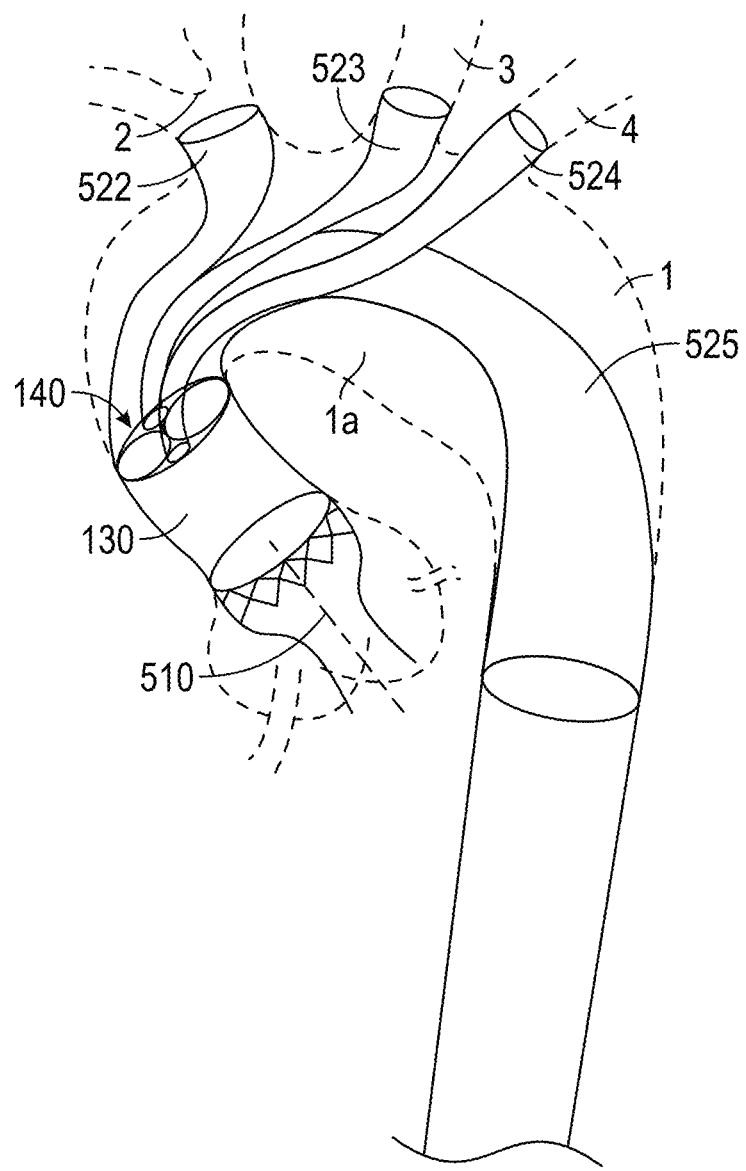
FIG. 21 shows a prostheses integrated with a heart valve.

FIG. 21 shows another example prostheses including a stent-graft 130 within an aortic arch 1 for bridging an aneurysm 1a. The prostheses can have the same structure as shown above in FIG. 19. According to the present example, the stent-graft 130 can be directly connected with and/or form a portion of a heart valve 510.

Figure 22:
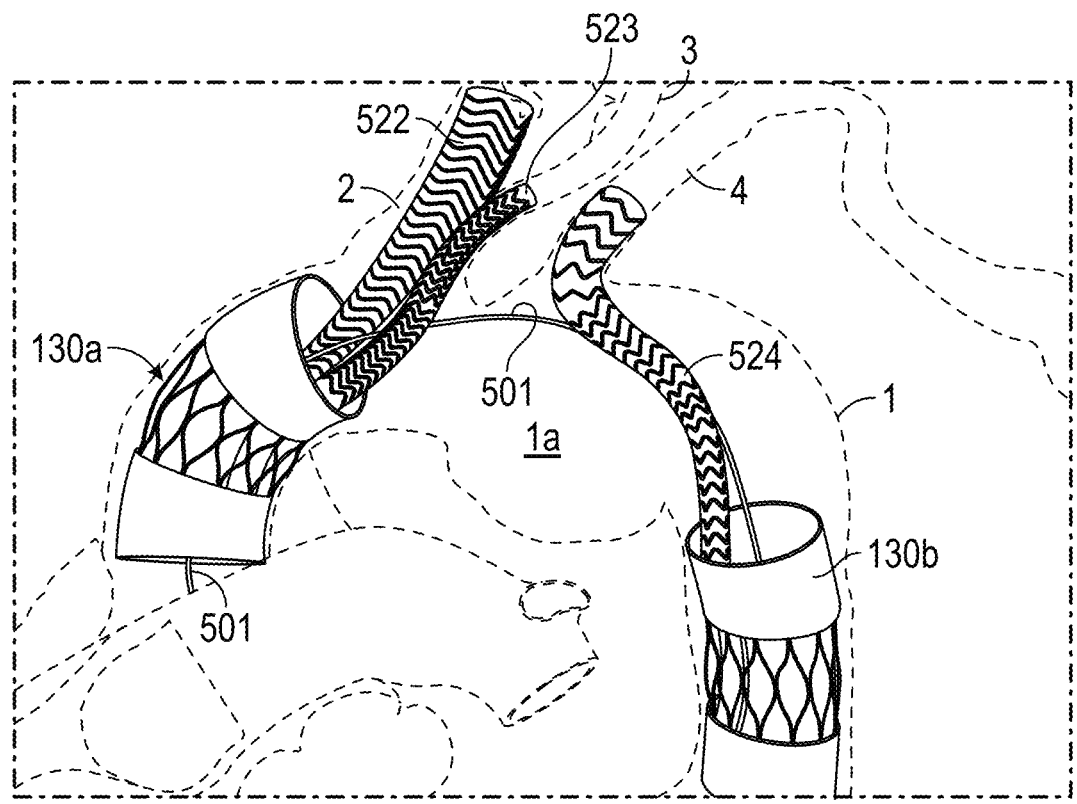
FIG. 22 shows an alternative prostheses including two stent-grafts for bridging an aortic aneurysm.
Figure 23:
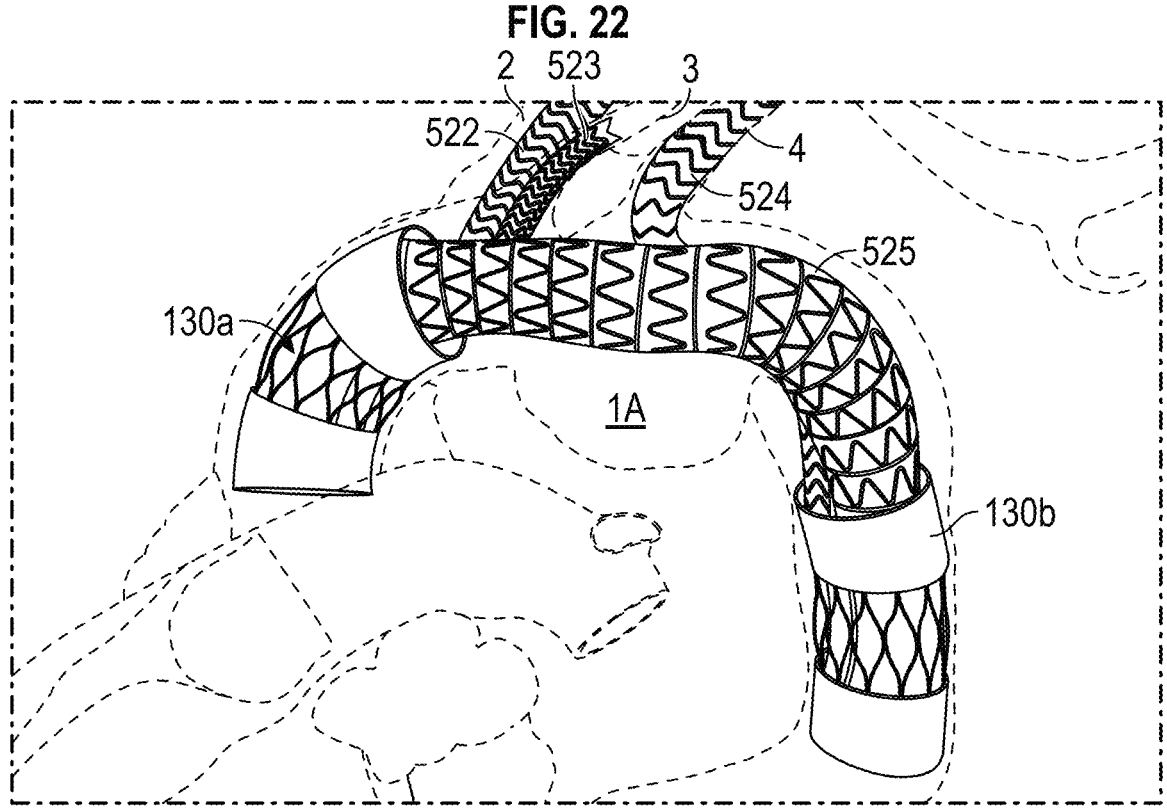
FIG. 23 shows the prostheses of FIG. 22 further showing a bridging, connecting stent-graft.

FIGS. 22-23 show another example prostheses including first and second stent-grafts 130a, 130b within an aortic arch 1 for bridging an aneurysm 1a. The stent-grafts 130a, 130b can be deployed as described above (e.g., one in the ascending aorta and one in the descending aorta). The two stent-grafts 130a, 130b can be positioned on opposite sides of the aneurysm 1a.

A guide wire and/or a catheter can be advanced through the brachiocephalic artery 2 (e.g., via either the right subclavian artery or the right common carotid artery) and into one of the channels 140 of the stent-graft 130a. A connecting stent-graft 522 can be deployed by the catheter 512. A first end of the connecting stent-graft 522 can be disposed and expanded within the channel 140 of the stent-graft 130a. A second end of the connecting stent-graft 522 can be disposed within the brachiocephalic artery 2. The connecting stent-graft 522 can thereby provide a fluid flow path for blood flow between the stent-graft 130a and the brachiocephalic artery 2.

Another guide wire and/or a catheter can be advanced through the left common carotid artery 3 and into another one of the channels 140 of the stent-graft 130a. A connecting stent-graft 523 can be deployed by the catheter. A first end of the connecting stent-graft 523 can be disposed and expanded within the channel 140 of the stent-graft 130a. A second end of the connecting stent-graft 523 can be disposed within the left common carotid artery 3. The connecting stent-graft 523 can thereby provide a fluid flow path for blood flow between the stent-graft 130a and the left common carotid artery 3.

Another guide wire and/or a catheter can be advanced through the left subclavian artery 4 and into another one of the channels 140 of the stent-graft 130b. A connecting stent-graft 524 can be deployed by the catheter. A first end of the connecting stent-graft 524 can be disposed and expanded within the channel 140 of the stent-graft 130b. A second end of the connecting stent-graft 524 can be disposed within the left subclavian artery 4. The connecting stent-graft 524 can thereby provide a fluid flow path for blood flow between the stent-graft 130b and the left subclavian artery 4.

Another guide wire and/or a catheter can be advanced within the aortic arch and through another one of the channels 140 of the stent-graft 130a and a channel 140 of the stent-graft 130b, such as the primary flow channel. Another connecting stent-graft 525 can be deployed by the catheter. A first end of the connecting stent-graft 525 can be disposed and expanded within the stent-graft 130a, such as within the channel 140. A second end of the connecting stent-graft 525 can be disposed and expanded within the channel 140 of the stent-graft 130b. The connecting stent-graft 525 can thereby provide a fluid flow path for blood flow between the stent-graft 130a and the stent-graft 130b and bridge the aneurysm 1a.

Figure 24A:
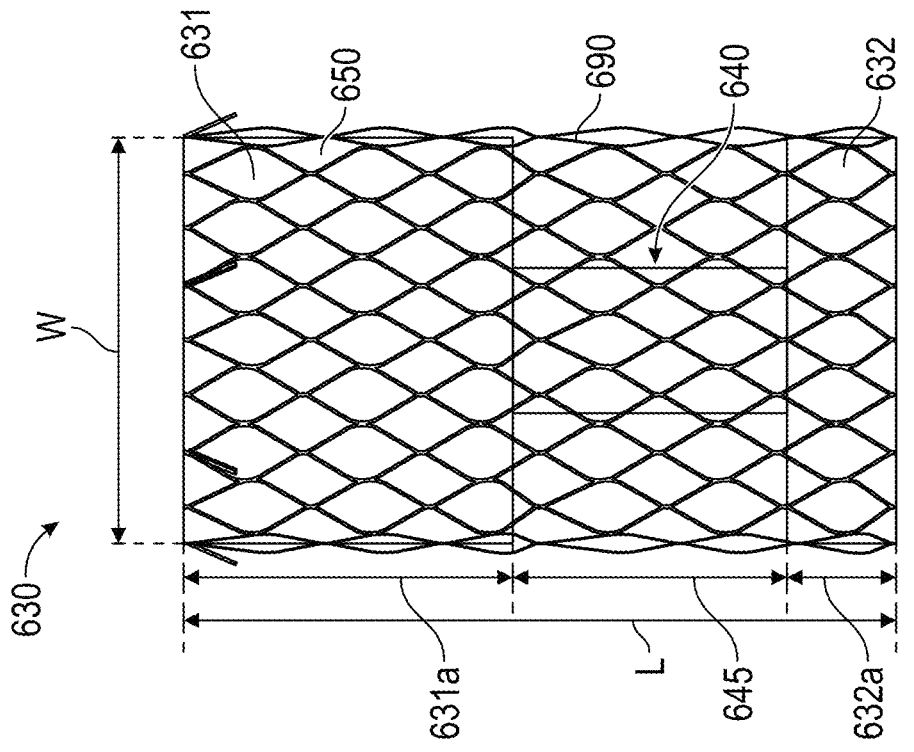
FIGS. 24A-B show front and side views of an alternative stent-graft including one extended-length open end.
Figure 24B:
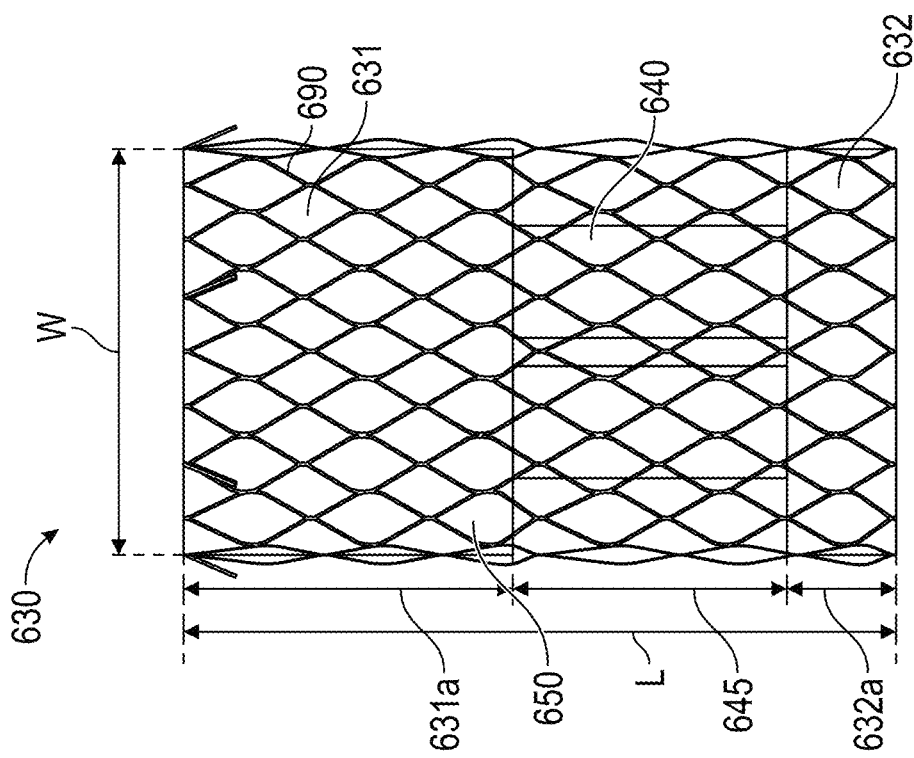

FIGS. 24A-B show an example of a multi-lumen stent-graft 630, like the stent-graft 130, but with the differences noted below. The stent-graft 630 can including a graft portion 650 and a stent portion 690. The stent portion 690 can comprise a shape and memory alloy such as super elastic nitinol or similar material. The graft portion 650 can be made of a single sheet or sheets of PTFE formed in a tube. The stent-graft 630 can include a first open end 631 and a second open end 632 opposite the first open end 631. The first end 631 and of the second end 632 can have a circular shape, although this is not required. The second end 632 can have the same shape as the first end 631, although this is not required. The first and second ends 631, 632 can include a base and an upper or lower rim.

The stent-graft 630 can have a diameter W. The stent-graft 630 can have a hub length L from the first end 631 to the second end 632. The hub length L can extend from an upper rim of the first end 631 to a lower rim of the second end 632. The hub length L can be between approximately 6 cm and 65 cm, depending on the application.

The first end 631 can have a length 631a. The length 631a can extend from the base to the upper rim. The second end 632 can have a length 632a. The length 632a can extend from the base to the lower rim. The lengths 631a, 632a can be different. Desirably, the length 631a can be greater than the length 631a. The length 631a can be between 2 and 5 times greater than the length 632a. This extended length can facilitate connection of a stent bridge deployed inside the first end 631. The length 631a can be between 40% and 70% of the hub length L.

The graft portion 650 can include a plurality of flow channels 640 that extend through the stent-graft 630. The channels 640 can provide fluid flow between the first end 631 and the second end 632. Each of the channels 640 can be sealed from the others of the channels 640. Each of the channels 640 can be formed of the graft portion 650. Each of the channels 640 can include an inlet on one end of the stent-graft 630 and an outlet on an opposite end of the stent-graft 630 (e.g., either on the first end 631 or the second end 632). Cylindrical walls of the first and second ends 631, 632 can offset the inlets/outlets of the channels 640 away from terminal rims of the respective first and second end 631, 632. Each of the channels 640 can be parallel with a longitudinal axis A of the stent-graft 630. The channels 640 can be unsupported by the self-expanding wire stent (i.e., between the first and second ends 631, 632). The channels 640 of the stent-graft 630 can include first and second channels. In other examples of stent-grafts more or fewer channels can be included. The number of channels can be based on the application, the planned prosthetic, and/or the location of use (e.g., aortic arch, thoracic aorta, or other).

The channels 640 can extend from the first open end 631 to the second open end 632 along a channel length 645. The channel length 645 can extend parallel with the longitudinal axis and/or the axes of the channels of the channels 640. The channel length 645 can extend from the cylindrical wall of the first end 631 to the cylindrical wall of the second end 632 (e.g., to the base of the cylindrical walls). Desirably, the channel length 645 can be between 40% and 70% of the hub length L or other ranges provided above.

Figure 25A:
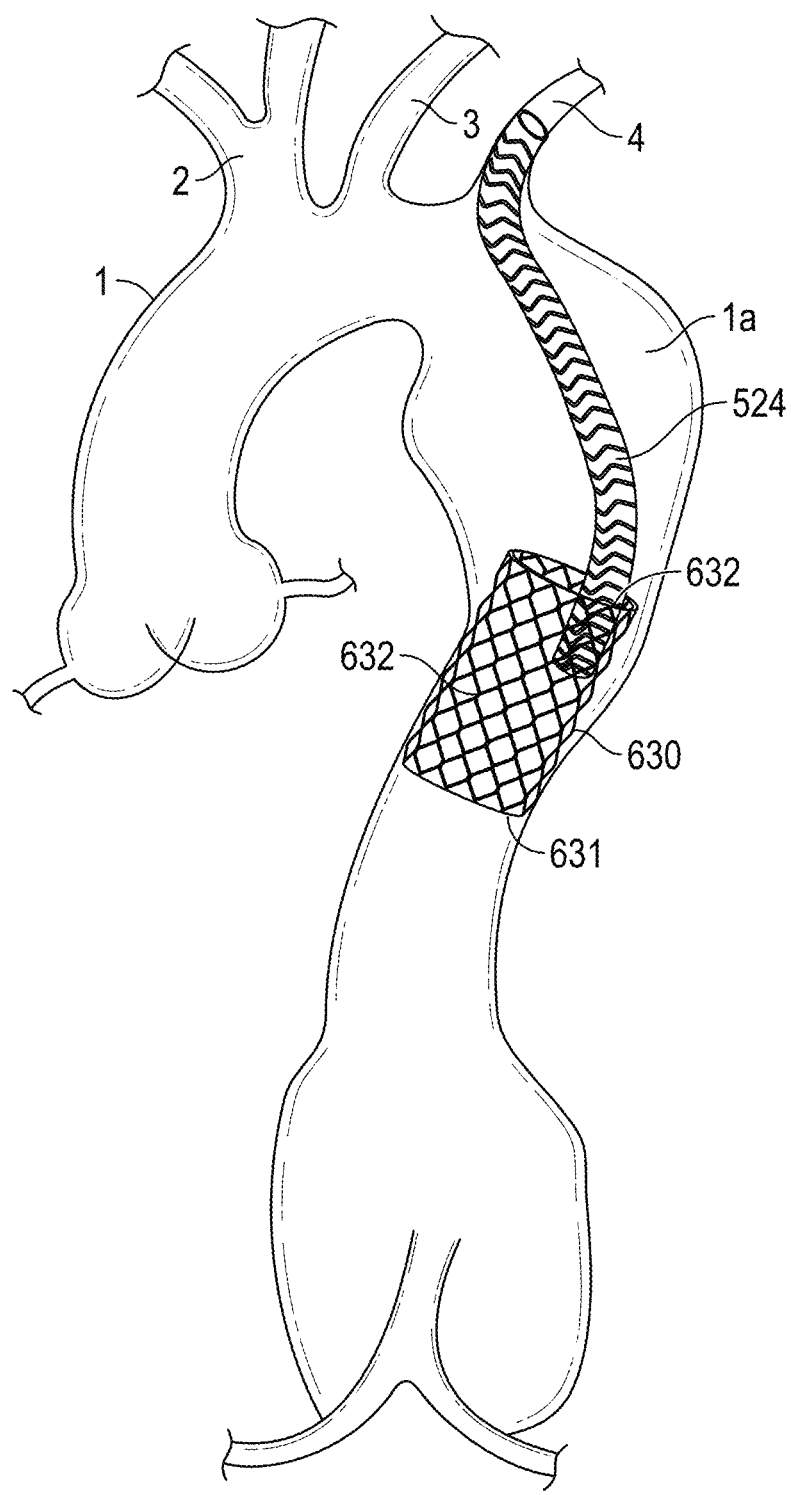
FIGS. 25A-C show deployment of a prostheses within the aorta to bridge an aortic aneurysm including multiple connecting stent-graft coupled within the stent-graft hub of FIG. 24.
Figure 25B:
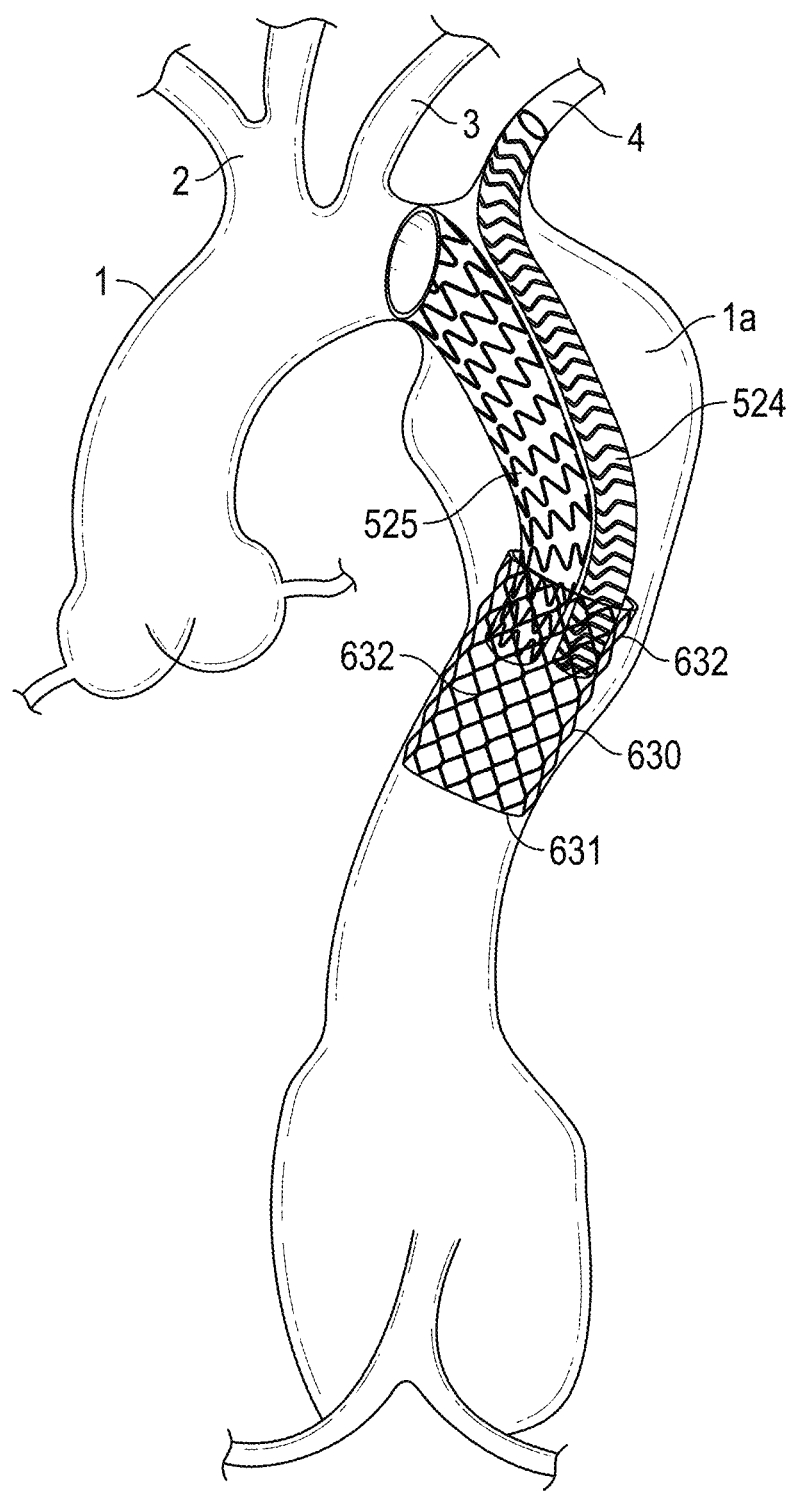
Figure 25C:
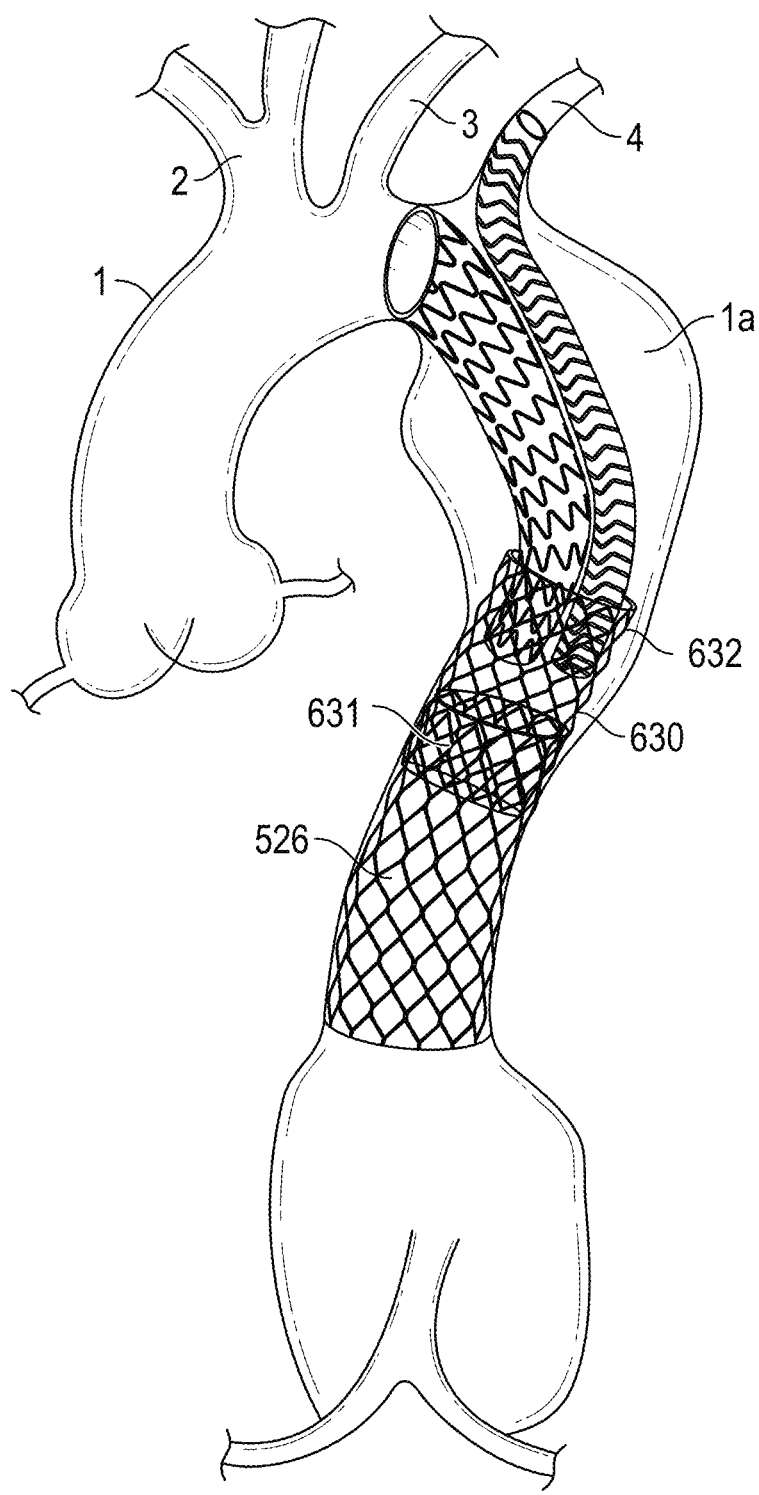
Figure 26:
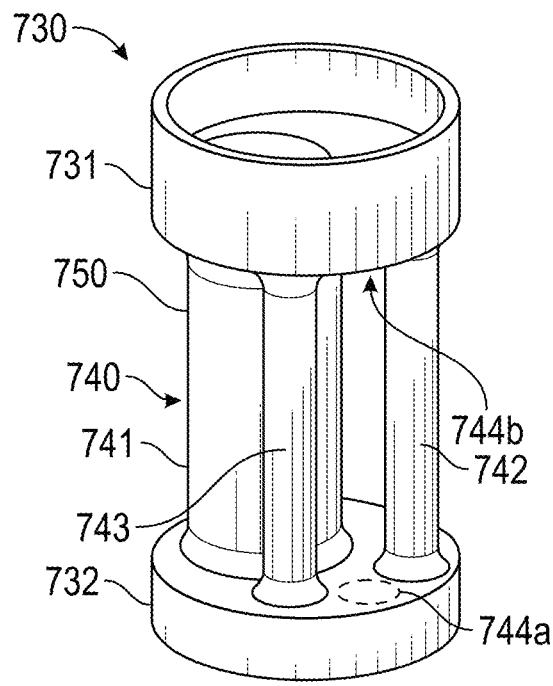
FIG. 26 shows a perspective view of an alternative stent-graft formed of woven Dacron.
Figure 27:
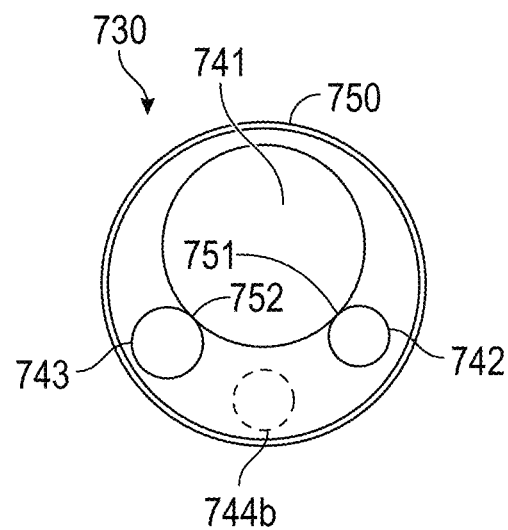
FIG. 27 shows a top view of the stent-graft of FIG. 26.
Figure 28:
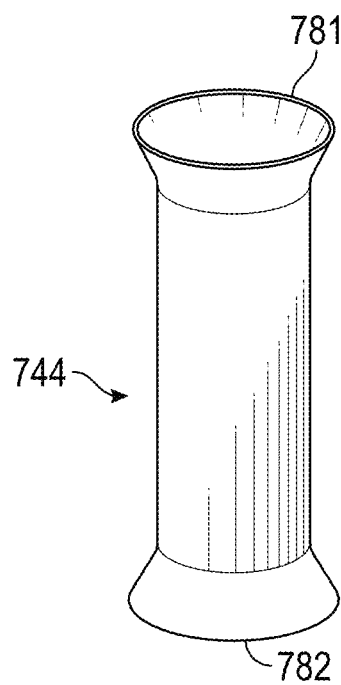
FIG. 28 shows a perspective view of an additional channel for the stent-graft of FIG. 26.
Figure 29:
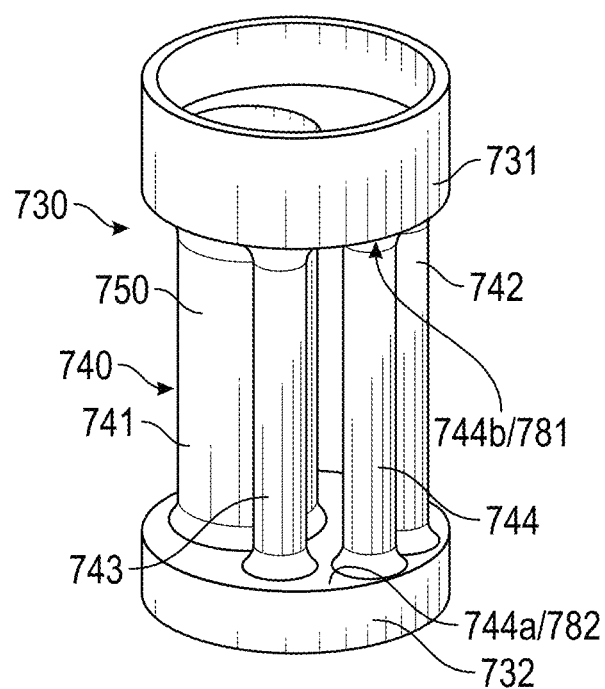
FIG. 29 shows the additional channel assembled with the stent-graft of FIG. 26.

FIGS. 25A-C shows another example prostheses including the stent-graft 630 within an aortic arch 1 for bridging an aneurysm 1a. As described above, a guide wire can be advanced in relation to the aneurysms 1a. A catheter carrying a collapsed stent-graft 630 can be advanced along the guide wire. The collapsed stent-graft 630 can be positioned relative to the aneurysm 1a and deployed using the catheter (e.g., above the aneurysm 1a and/or within the descending aorta). The first end 631 of the stent graft 630 can be distal to the second end 632 and extend towards the thoracic aorta.

A guide wire and/or a catheter can be advanced through any of the branch arteries 2-4 and into one of the channels 640 of the stent-graft 630 through the second end 632. A connecting stent-graft 524 can be deployed by the catheter with a first end of the connecting stent-graft 524 disposed within a channel 640 of the stent-graft 630. A second end of the connecting stent-graft 524 can be disposed within the branch artery 2-4. The connecting stent-graft 524 can thereby provide a fluid flow path for blood flow between the stent-graft 630 and the branch artery. Another guide wire and/or a catheter can be advanced within the aortic arch and through another one of the channels 640 of the stent-graft 630, such as a primary flow channel. Another connecting stent-graft 525 can be deployed by the catheter. A first end of the connecting stent-graft 525 can be disposed within aorta, such as within the aortic arch. A second end of the connecting stent-graft 525 can be disposed within the channel of the channels 640. The connecting stent-graft 525 can thereby provide a fluid flow path for blood flow between the stent-graft 630 and the aorta and bridge the aneurysm 1a.

Another guide wire and/or a catheter can be advanced within the aorta (e.g., from the thoracic aorta) and into the first end 631 of the stent-graft 630. A bridge stent-graft 526 can be deployed by the catheter. The bridge stent-graft 526 can be generally formed as a tube of graft material with or without a self-expanding stent. The diameters and length of the bridge stent-graft 526 can be selected based on the planned placement within the prostheses. For example, the length of the stent-graft 526 may be selected to bridge another aneurism within the descending aorta 1. A first end of the connecting stent-graft 525 can be disposed within the first end 631 of the stent graft 630. The first end of the connecting stent-graft 525 can be radially expanded within the first end 631 of the stent graft 630. The connecting stent-graft 525 can serve to elongate the first end 631. A second end of the connecting stent-graft 526 can be disposed within aorta, such as within the descending aortic arch or into the thoracic aorta. The connecting stent-graft 526 can thereby provide a fluid flow path for blood flow between the stent-graft 630 and the descending aorta.

FIGS. 26-29 show an example of a multi-lumen stent-graft 730, like the stent-graft 130 but with the differences noted below. The stent-graft 730 can include a graft portion 750 and a stent portion (not shown). Desirably, the graft portion 750 can be made of a sheet of woven Dacron. The stent-graft 730 can include a first open end 731 and a second open end 732 opposite the first open end 731. The graft portion 750 can include the plurality of flow channels 740 that extend through the stent-graft 730. The channels 740 can provide fluid flow between the first end 731 and the second end 732. The channels 740 can be formed of a single tube of the woven Dacron material. Each of the channels 740 can be separated from the others of the channels 740 by one or more suture lines 751, 752 of the Dacron material. The channels 740 of the stent-graft 730 can include first, second, and third channels, 741-743. Alternatively, other numbers of channels can be included in the channels 740.

The stent-graft 730 can further include an additional channel 744. The channel 744 can be formed separately from the graft portion 750. The channel 744 can be formed by suturing, adhesive, woven material or other means. The channel 741 can include a first end 781 and a second end 782. The first and/or second ends 781, 782 can include excess or flared material. The first and second ends 731, 732 can include apertures 744*a*, 744*b* within the graft portion 750. The apertures 744*a*, 744*b* can have diameters corresponding to diameters of the ends 781, 782. The ends 781, 782 can be attached over the apertures 744*a*, 744*b* to form one of the channels 740 extending from the first end 131 to the second end 132. The ends 781, 782 can be attached with the graft portion 750 by suturing, adhesives and/or other mechanical means.

Certain Terminology

Terms of orientation used herein, such as "top," "bottom," "upper," "lower," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

Summary

Several illustrative examples of stent-grafts and related surgeries have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

Any portion of any of the steps, processes, structures, and/or devices disclosed or illustrated in one example in this disclosure can be combined or used with (or instead of) any other portion of any of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification can be included in any example.

In summary, various examples of stent-grafts and related methods have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

What is claimed is:

1. A multi-lumen expandable stent-graft comprising:
a graft sleeve formed of a single tube of polymer material having a sleeve diameter and comprising:
  a first open end including a first cylindrical wall having an upper rim;
  a second open end including a second cylindrical wall having a lower rim, the first open end spaced apart from the second open end along a longitudinal axis,
  a hub length extending from the upper rim of the first open end to the lower rim of the second open end, the hub length between 4 and 9 cm; and
  a plurality of parallel flow channels extending between the first open end and the second open end and defining a channel length therebetween, the channel length being between 50% and 90% of the hub length, the plurality of parallel flow channels including:
    a first flow channel formed by a first linear connected segment of the polymer material channel and including inlet and outlet ports in communication with the respective first and second open ends of the graft sleeve, the first linear connected segment aligned parallel with the longitudinal axis of the stent-graft, the first linear connected segment having a first width;
    a second flow channel formed by a second linear connected segment of the polymer material channel and including inlet and outlet ports in communication with the respective first and second open ends of the graft sleeve, the second linear connected segment aligned parallel with the longitudinal axis of the stent-graft, the second linear connected segment having a second width;
    a third flow channel formed by a third linear connected segment of the polymer material channel and including inlet and outlet ports in communication with the respective first and second open ends of the graft sleeve, the third linear connected segment aligned parallel with the longitudinal axis of the stent-graft, the third linear connected segment having a third width;
    a fourth flow channel formed by a the first, second, and third linear connected segments of the polymer material channel and including inlet and outlet ports in communication with the respective first and second open ends of the graft sleeve;
a self-expanding wire stent coaxially mounted over the graft sleeve and affixed to said graft sleeve at the first cylindrical wall of the first open end and the second cylindrical wall of the second open end;
wherein the polymer material of the graft sleeve comprises Polytetrafluoroethylene (PTFE) and the first, second, and third linear connected segments comprise fused portions of the PTFE material;
wherein a summation of 1) a circumference of each of the first, second, third and fourth flow channels and 2) twice a sum of the first, second, and third widths of the respective first, second, and third linear connected segments is equal to a circumference of the single tube of polymer material; and
wherein a first diameter of the first flow channel is within 5% to 25% of the sleeve diameter, a second diameter of the second flow channel is within 5% to 25% of the sleeve diameter, a third diameter of the third flow channel is within 5% to 25% of the sleeve diameter, and a fourth diameter of the fourth flow channel is within 50% to 75% of the sleeve diameter.

2. A multi-lumen expandable stent-graft comprising:
a graft sleeve comprising polymer material forming first, second and third flow channels between a first open end and a second open end;
a self-expanding wire stent coaxially mounted over the graft sleeve and affixed to said graft sleeve at the first and second open ends;
wherein the first flow channel is formed by a first linear connected segment of the polymer material channel, the first linear connected segment aligned parallel with a longitudinal axis of the stent-graft, and includes inlet and outlet ports spaced inwardly from the first and second open ends of the graft sleeve;
wherein the second flow channel is formed by a second linear connected segment of the polymer material channel, the second linear connected segment aligned parallel with the longitudinal axis of the stent-graft, and includes inlet and outlet ports spaced inwardly from the first and second open ends of the graft sleeve;
wherein the third flow channel is formed by a third linear connected segment of the polymer material channel, the third linear connected segment aligned parallel with the longitudinal axis of the stent-graft, and includes inlet and outlet ports spaced inwardly from the first and second open ends of the graft sleeve;

wherein a first diameter of the first flow channel is within 10% to 40% of a sleeve diameter of the first and second open ends, a second diameter of the second flow channel is within 10% to 40% of the sleeve diameter, and a third diameter of the third flow channel is within 50% to 80% of the sleeve diameter.

3. The stent-graft of claim 2, wherein a channel length of the first, second, and third channels is between 50% and 90% of a hub length extending from an upper rim of the first open end to a lower rim of the second open end.

4. The stent-graft of claim 2, wherein a channel length of the first, second, and third channels is between 75% and 90% of a hub length extending from an upper rim of the first open end to a lower rim of the second open end.

5. The stent-graft of claim 2, wherein the first, second, and third channels are parallel.

6. The stent-graft of claim 2, wherein the first, second, and third flow channels are unsupported by the self-expanding wire stent.

7. The stent-graft of claim 2, wherein the first and second open ends each include a cylindrical wall portion supported by the self-expanding wire stent.

8. The stent-graft of claim 7, wherein the cylindrical wall of the first open end has a length that is between 2 and 5 times greater than a length of the cylindrical wall of the second open end.

9. The stent-graft of claim 2, wherein respective ends of the first, second, and third linear connected segments are spaced inwardly from the first and second open ends.

10. The stent-graft of claim 2, wherein the first and second open ends include folded portions of the polymer material.

11. The stent-graft of claim 2, wherein the first and second open ends include an additional layer of the polymer material that encapsulates first and second ends of the graft sleeve.

12. The stent-graft of claim 2, wherein the graft sleeve comprises a single tube of the polymer material and a total circumference of each of the flow channels is equal to a circumference of the single tube of polymer material.

13. The stent-graft of claim 2, wherein the polymer material of the graft sleeve comprises Polytetrafluoroethylene (PTFE) and the first, second, and third linear connected segments comprise fused portions of the PTFE material.

14. The stent-graft of claim 13, wherein the fused portions of the PTFE material are formed by melting the PTFE material above a melting temperature thereof.

15. The stent-graft of claim 13, wherein the fused portions of the PTFE material are formed by ultrasonic welding.

16. The stent-graft of claim 13, wherein the fused portions of the first linear connected segment includes an intermediate layer of PTFE material.

17. A multi-lumen expandable stent-graft comprising:
a graft sleeve comprising polymer material forming first, second and third flow channels between a first open end and a second open end;
a self-expanding wire stent coaxially mounted over the graft sleeve and affixed to said graft sleeve at the first and second open ends;
wherein the first flow channel is formed by a first linear connected segment of the polymer material channel, the first linear connected segment aligned parallel with a longitudinal axis of the stent-graft, and includes inlet and outlet ports spaced inwardly from the first and second open ends of the graft sleeve;
wherein the second flow channel is formed by a second linear connected segment of the polymer material channel, the second linear connected segment aligned parallel with the longitudinal axis of the stent-graft, and includes inlet and outlet ports spaced inwardly from the first and second open ends of the graft sleeve;
wherein the third flow channel is formed by a third linear connected segment of the polymer material channel, the third linear connected segment aligned parallel with the longitudinal axis of the stent-graft, and includes inlet and outlet ports spaced inwardly from the first and second open ends of the graft sleeve;
a fourth flow channel, wherein a first diameter of the first flow channel is within 5% to 25% of a sleeve diameter of the first and second open ends, a second diameter of the second flow channel is within 5% to 25% of the sleeve diameter, a third diameter of the third flow channel is within 5% to 25% of the sleeve diameter and a fourth diameter of the fourth flow channel is within 50% to 75% of the sleeve diameter.

* * * * *

UNITED STATES PATENT AND TRADEMARK OFFICE
CERTIFICATE OF CORRECTION

PATENT NO. : 11,324,583 B1
APPLICATION NO. : 17/497199
DATED : May 10, 2022
INVENTOR(S) : Pierre Galvagni Silveira It is certified that error appears in the above-identified patent and that said Letters Patent is hereby corrected as shown below:

In the Specification

In Column 6, Line 3, delete "herein" and insert --herein.--.

In Column 10, Line 26, delete ")." and insert --)).--.

In the Claims

In Column 22, Line 17, In Claim 1, delete "a the" and insert --the--.

Signed and Sealed this
Twenty-seventh Day of August, 2024

Katherine Kelly Vidal
*Director of the United States Patent and Trademark Office*